US011931471B2

(12) United States Patent
An et al.

(10) Patent No.: US 11,931,471 B2
(45) Date of Patent: Mar. 19, 2024

(54) SHOE MANAGEMENT DEVICE

(71) Applicant: LG ELECTRONICS INC., Seoul (KR)

(72) Inventors: Seong Woo An, Seoul (KR); Seok Kyu Kang, Seoul (KR); Heesu Yang, Seoul (KR); Min Kyu Oh, Seoul (KR); Suyoung Lee, Seoul (KR); Ja Yoen Kim, Seoul (KR); Hwayun Choi, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 731 days.

(21) Appl. No.: 17/073,532

(22) Filed: Oct. 19, 2020

(65) Prior Publication Data

US 2021/0220497 A1  Jul. 22, 2021

Related U.S. Application Data

(60) Provisional application No. 62/993,205, filed on Mar. 23, 2020.

(30) Foreign Application Priority Data

Jan. 17, 2020  (KR) .......................... 10-2020-0006858

(51) Int. Cl.
*A47L 23/20* (2006.01)
*A61L 2/10* (2006.01)
(Continued)

(52) U.S. Cl.
CPC ............... *A61L 2/10* (2013.01); *A47L 23/205* (2013.01); *A61L 2/26* (2013.01); *A61L 2/24* (2013.01);
(Continued)

(58) Field of Classification Search
None
See application file for complete search history.

(56) References Cited

U.S. PATENT DOCUMENTS

| 5,165,181 A | 11/1992 | Acosta, Sr |
| 5,369,892 A | 12/1994 | Dhaemers |

(Continued)

FOREIGN PATENT DOCUMENTS

| JP | 09-065940 | 3/1997 |
| KR | 20-0253977 | 11/2001 |

(Continued)

OTHER PUBLICATIONS

U.S. Appl. No. 17/073,511, filed Oct. 19, 2020.

(Continued)

*Primary Examiner* — Levon J Shahinian
(74) *Attorney, Agent, or Firm* — KED & ASSOCIATES, LLP

(57) ABSTRACT

A shoe management device may have a housing having a body to define an inner space and a cover to open or close the body to allow access to the inner space. Agitators may be provided at a bottom of the body, which may be configured to hold shoes, and the agitators may remove foreign matter from the shoes. An upper portion of the body may have an air generator configured to blow air toward the shoes to remove foreign matter. In addition, moisture and germs inside the shoe may be removed by hot air, ultraviolet light, and plasma ions provided by a care assembly provided inside of the body and configured to be at least partially inserted into the shoes.

18 Claims, 15 Drawing Sheets

(51) Int. Cl.
*A61L 2/24* (2006.01)
*A61L 2/26* (2006.01)

(52) U.S. Cl.
CPC ..... *A61L 2202/122* (2013.01); *A61L 2202/14* (2013.01); *A61L 2202/26* (2013.01)

(56) References Cited

U.S. PATENT DOCUMENTS

| | | | |
|---|---|---|---|
| 6,845,569 | B1 | 1/2005 | Kim |
| 2011/0048474 | A1 | 3/2011 | Kim |
| 2018/0154028 | A1* | 6/2018 | Offutt .................. A61L 2/24 |
| 2021/0071950 | A1 | 3/2021 | Ohnari |
| 2021/0401260 | A1 | 12/2021 | Youn |

FOREIGN PATENT DOCUMENTS

| | | |
|---|---|---|
| KR | 20-0283178 | 7/2002 |
| KR | 20-0393879 | 8/2005 |
| KR | 10-2007-0034807 | 3/2007 |
| KR | 10-2008-0055288 | 6/2008 |
| KR | 20-2009-0001858 | 2/2009 |
| KR | 10-1053100 | 8/2011 |
| KR | 20-2011-0011365 | 12/2011 |
| KR | 10-1260063 | 4/2013 |
| KR | 10-2012-0122910 | 10/2014 |
| KR | 10-2014-0124216 | 10/2014 |
| KR | 10-1955719 | 3/2019 |
| KR | 10-2037612 | 11/2019 |
| WO | WO 2010/093173 | 8/2010 |

OTHER PUBLICATIONS

U.S. Appl. No. 17/073,532, filed Oct. 19, 2020.
International Search Report dated Dec. 30, 2020 issued in Application No. PCT/KR2020/012437.
International Search Report dated Dec. 8, 2020 issued in Application No. PCT/KR2020/012434.
U.S. Office Action dated Nov. 21, 2023 issued in U.S. Appl. No. 17/073,511.

* cited by examiner

SHOE MANAGEMENT DEVICE

CROSS-REFERENCE TO RELATED APPLICATION(S)

The present application claims priority to Korean Patent Application No. 10-2020-0006858, filed in Korea on Jan. 17, 2020, and U.S. Provisional Application No. 62/993,205, filed in the United States on Mar. 23, 2020, the entire contents of which are incorporated herein by reference.

BACKGROUND

1. Field

The present disclosure relates to a shoe management device.

2. Background

Shoes are necessary items in modern life, and most modern people, especially city dwellers, wear shoes all day. In many cases, a single pair of shoes is often used continuously for many days.

There are various types of shoes, but people living in urban areas usually wear shoes that cover an entirety of each foot. After being worn all day, body fluids such as foot sweat remain inside if the shoes, and increasing humidity and body temperature may cause many bacteria to breed and multiply inside the shoes and generate odor.

In addition, dirt, dust, and various foreign substances may smear the bottoms or outer surfaces of shoes. Such foreign substances increase aging of the shoes and cause a messy appearance. Generally, dirt or foreign matter of a relatively large particle size attaches to the bottom of the shoes, while moisture, fine dirt, or dust attaches to an exterior surface of the shoes.

While many devices for shoe management have been developed, but the related art does not simultaneously remove dirt, dust, foreign matter, bacteria, odor, and moisture. For example, Korean Patent Application No. 10-2012-0122910 discloses a device capable of removing moisture and odor in shoes, but the device cannot remove dust on the exterior of the shoes.

Korean Utility Model Registration No. 20-0393879 discloses insert members inserted into shoes for hygiene management and that have a dehumidifying function, an antibacterial function, a deodorizing function, and a fragrance diffusion function, but the disclosed insert members do not have the function of removing dust on the exteriors of the shoes. The same problem remains even in Korean Utility Model Registration No. 20-0283178 and Korean Utility Model Application Publication No. 20-2009-0001858.

A device proposed in Korean Patent Application Publication No. 10-2008-0055288 has a sterilization function using a photocatalyst and a drying function using a heater. However, the device cannot remove dust on the exteriors of the shoes, and is not suitable for home use due to the large size thereof.

The above references are incorporated by reference herein where appropriate for appropriate teachings of additional or alternative details, features and/or technical background.

BRIEF DESCRIPTION OF THE DRAWINGS

Embodiments will be described in detail with reference to the following drawings in which like reference numerals refer to like elements, and wherein.

DETAILED DESCRIPTION

Figure 1:
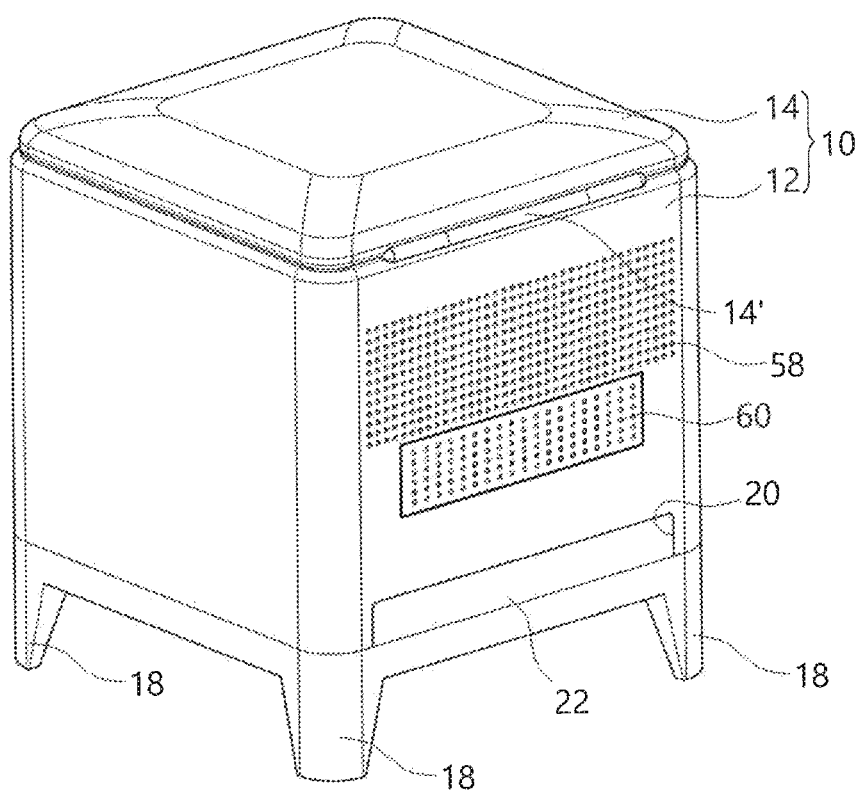
FIG. 1 is a perspective view illustrating an appearance of a shoe management device according to an embodiment of the present disclosure.

In the drawings, the embodiments of a shoe management device or shoe care device of the present disclosure are illustrated. As illustrated in FIG. 1, a housing or case 10 may constitute an exterior appearance of the shoe management device according to a first exemplary embodiment of the present disclosure. The housing 10 may include a housing body 12, and a cover or lid 14 covering an open upper portion of the housing body 12. In the embodiment, the housing body 12 may have a hexahedral shape, and may have an inner space 16 (FIG. 2) therein so that at least one shoe is inserted thereinto. The inner space 16 may be opened and/or closed by the cover 14. The cover 14 may have a hinge 14' at an end portion thereof as illustrated in FIGS. 1 and 3 and may open and/or close the inner space 16 by being rotated relative to the hinge 14'.

The housing 10 may have a hexahedral shape as a whole, and a user may sit on the cover 14. Accordingly, the housing 10 may function as a chair, bench, or storage ottoman. The user may take out managed shoes from the inner space 16, cover the cover 14, and may put the shoes on or get dressed while sitting on the cover 14. Although a hexahedral or cuboid shape is shown in the figures, a shape of the housing 10 is not limited. The housing 10 may have any shape with a cover 14 having a relatively flat surface so as to support a sitting user. For example, the housing 10 may be cylindrical. The cover 14 may have an optional cushion provided on a top surface to provide comfort. An body 12 and cover 12 may be designed with various materials, prints, images, etc. to have various appearances (e.g., to resemble a Moroccan pouf, a wooden stool or footrest, or a sleek, modern bench). A length or width of the housing 10 may be 420 mm (roughly 1.3 feet), but embodiments disclosed herein are not limited.

Legs 18 may be provided on a lower end portion or bottom of the housing 10. The legs 18 may allow the cover 14 to have at least a predetermined height from a ground or floor surface on which the housing 10 is provided. A length of each of the legs 18, along with a height of the body 12, may be preset or predetermined such that the height of the cover 14 from the ground may be the height of a normal chair or stool (e.g., 16-23 inches). When a height of the housing 10 is relatively low, the legs 18 may be arranged beneath the housing 10 so that the housing 10 may function as a chair. When the height of the housing 10 is relatively high, the legs 18 may be made to have a relatively short length or may not be arranged beneath the housing 10 so that the housing 10 may function as a chair.

A tray opening 20 may be formed in a lower portion of an outer surface of the housing 10. A tray 22 to collect foreign matter falling from shoes inside of the housing 10 may be inserted into and withdrawn from the tray opening 20, similar to a drawer configuration. The tray 22 may be provided at the bottom of the inner space 16 when inserted into the tray opening 20 and may be configured to occupy almost an entire bottom of the inner space 16. Foreign matter removed from the shoe by the operation of agitators 32 (FIG. 2) described later may collect in the tray 22.

The legs 18 may hold the housing 10 above the ground, and the housing 10 may have a light emitting device panel to project a light display on the ground that shows time, operation status, etc. A side of the housing 10 may have a user interface (e.g., buttons) to turn on the housing 10 and to control a management of the shoes inside.

Figure 2:
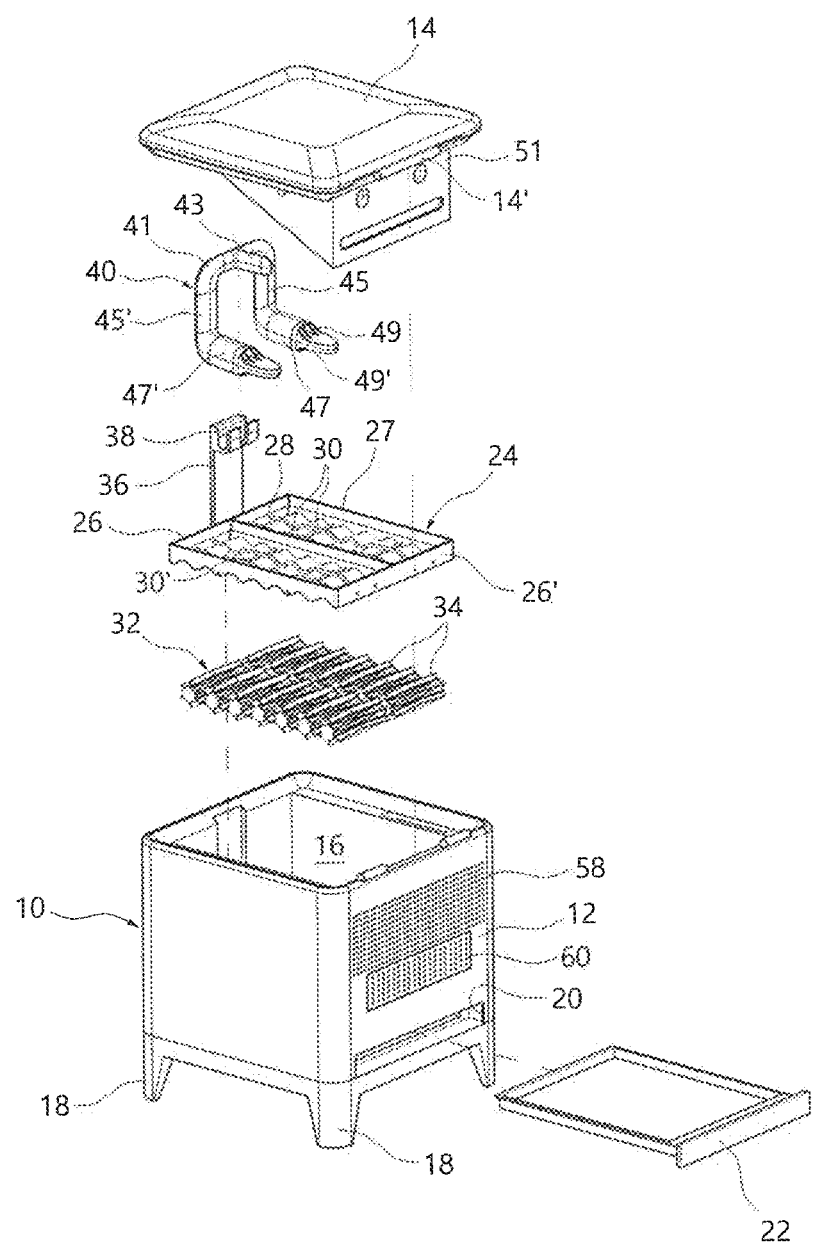
FIG. 2 is an exploded perspective view illustrating components of the shoe management device illustrated FIG. 1.
Figure 3:
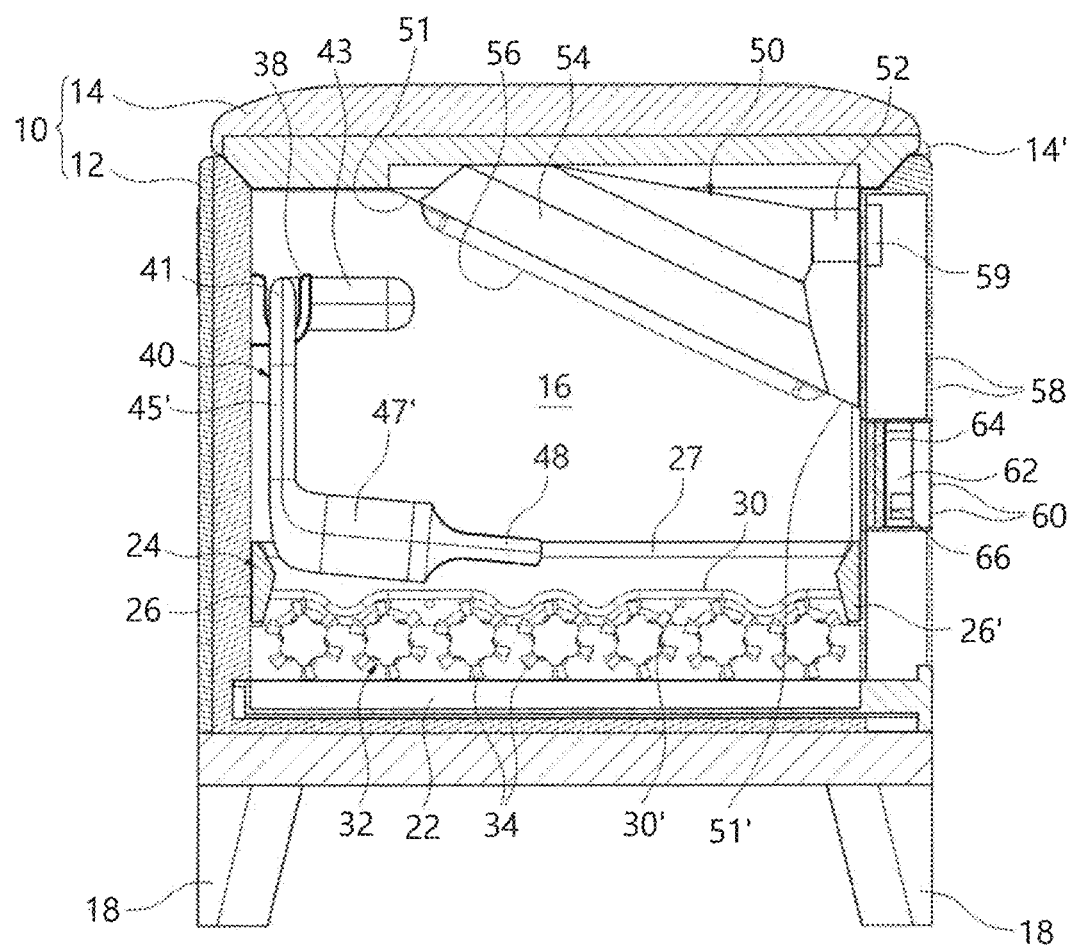
FIG. 3 is a sectional view illustrating the inside of the shoe management device illustrated in FIG. 1.
Figure 5:
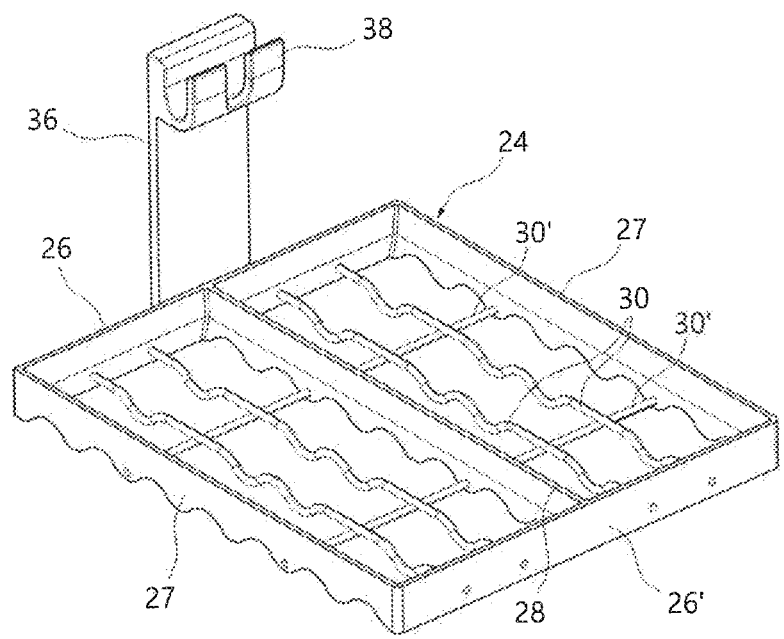
FIG. 5 is a perspective view illustrating an internal frame of the shoe management device illustrated in FIG. 1.
Figure 6:
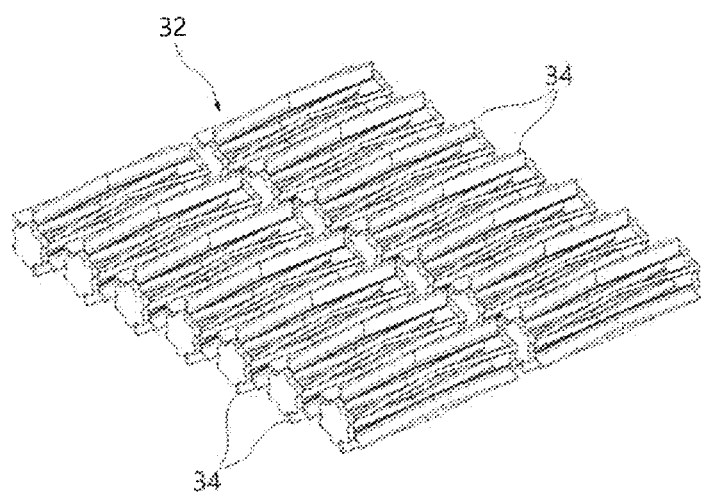
FIG. 6 is a perspective view illustrating the configuration of agitators of the shoe management device illustrated in FIG. 1.
Figure 7:
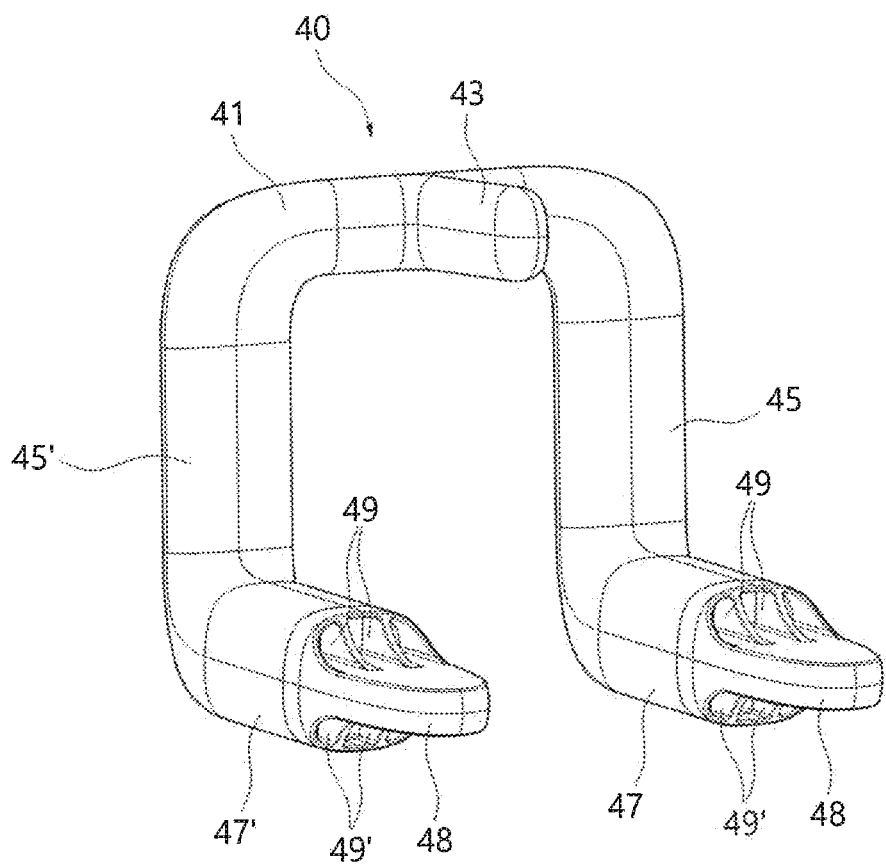
FIG. 7 is a perspective view illustrating the configuration of a care unit of the shoe management device illustrated in FIG. 1.

Referring to FIGS. 1-2, an internal frame 24 may surround or extend along an inner surface of the lower end of the inner space 16 of the housing 10. When the housing 10 has a hexahedral or cuboid shape, the internal frame 24 may be configured in a rectangular or square grid shape as illustrated in FIGS. 2 and 5. The internal frame 24 may have a first end member or plate 26 and a second end member or plate 26' extending parallel to each other. Two side end members or plates 27 may connect the first end member 26 and the second end member 26' to each other to form the rectangular or square shape. The internal frame 24 may be mounted in the housing 10 by surrounding the inner surface of the lower end of the inner space 16. Inner surfaces of side walls of the housing 10 may contact outer side surfaces of the first and second end members 26 and 26' and the side end members 27.

A dividing member or plate 28 may be provided to connect middle or central portions of the first end member 26 and the second end member 26' to each other. A right shoe and a left shoe may be located at opposite sides (e.g., a right side and a left side, respectively) of the dividing member 28 relative thereto. Multiple curved grooves 27' may be formed in the lower ends of the side end members 27 to prevent or reduce interference of the side end members 27 with the agitators 32 and to facilitate contact between the removal ribs 34 described later and the bottoms and outer surfaces of the shoes.

A support grid may be formed by multiple first support members or supports 30 intersecting multiple second support members or supports 30' in the internal frame 24. The first support members 30 and the second support members 30' may be configured to be orthogonal to each other. Opposite ends of the first support member 30 may be coupled to the first end member 26 and the second end member 26', and opposite ends of the second support member 30' may be coupled to the side end members 27. The second support member 30' may be provided by passing through the dividing member 28. A shoe may be supported by the first support member 30 and the second support member 30', and may not be directly supported by the agitators 32 described below. Curved portions may be provided in the first support member 30, and each of the curved portions may be located in a gap between the agitators 32.

Multiple agitators 32 may be mounted in a space defined by the internal frame 24. Each of the agitators 32 may have a cylindrical shape, and multiple removal ribs 34 may be provided around an outer circumference of the agitator. The removal ribs 34 may be made of elastic materials and be provided at predetermined angular intervals on the outer circumference of the agitator 32. The removal ribs 34 may move while being in close contact with a lower surface and outer surface of the shoe by the rotation of the agitator 32 and remove foreign matter on the shoe. As shown in the drawings, four removal ribs 34 may be provided on each agitator 32, but a number of the removal ribs 34 is not limited and may vary. Each of the removal ribs 34 may not be straight, but may be curved or inclined to more efficiently remove foreign matter on the shoe.

Embodiments disclosed herein are not limited to the agitators 32, which are not required and may be omitted or turned off. For example, when foreign matter on the lower surface and side surfaces of the shoe are not required to be removed, the agitators 32 may not be used so as not to rotate.

The agitators 32 may extend parallel to the first end member 26 and the second end member 26', and may be provided at opposite sides of the dividing member 28 relative thereto. Accordingly, multiple agitators 32 may be arranged in two columns between the first end member 26 and the second end member 26'. The multiple agitators 32 may be connected to a gear train, and may be driven by using power generated by one or two driving sources. For convenience, configuration for the driving of the agitator 32 is not shown. The agitators 32 adjacent to each other in one column may be rotated in directions opposite to each other. Accordingly, rotational forces of the agitators 32 may not be applied to a shoe only in one direction, so the shoe may be prevented from moving in one direction inside the inner space 16. As an alternative, the agitators 32 may vibrate to shake off foreign matter from the shoes.

A holding column 36 may be mounted to the internal frame 24 or the inner surface of the housing 10 at a rear. The height of the holding column 36 may be adjusted inside the housing 10. The height of the holding column 36 may be manually adjusted, or may be automatically adjusted by a motor. Configuration for the height adjustment of the holding column 36 is not illustrated for convenience. A hook 38 may be provided on a front end of the holding column 36. A care unit or assembly 40 may be hung on the hook 38. The care unit 40 may comprise a shoe rack, shoe hanger, or shoe holder, which may be a shoe dryer that includes a blower, a sterilizer, and/or a plasma ion generator. The care unit 40 may be removable.

When viewed from the front, the care unit 40 may have a handle or protrusion 43 protruding from a center or middle of a body part or frame 41 toward the front. Extension parts or downward extensions 45 and 45' may be provided by extending downward at opposite ends of the body part 41, and operation performance parts or heads 47 and 47' may protrude at the front ends of the extension parts 45 and 45', respectively, in the same direction as the protruding direction of the handle 43 (i.e., forward). The operation performance parts 47 and 47' may alternatively be referred to as forward extensions or forward protrusions. The operation performance parts 47 and 47' may perform various functions of the care unit 40, and may be configured to be inserted into shoes.

Referring to FIGS. 2-9, a sterilization emitter or sterilizer 48 may be provided on each of the front ends of the operation performance parts 47 and 47'. For example, the sterilization emitter 48 may include at least one ultraviolet (UV) light emitting diode (LED). The sterilization emitter 48 may emit ultraviolet light such as UV-C light (for example, light having a wavelength between 220 nm and 280 nm) intended to kill or inactivate bacteria or other microorganisms. The sterilization emitter 48 may prevent microorganisms from propagating or multiplying by sterilization, and may also have an odor prevention effect. The sterilization emitter 48 may kill or inactivate bacteria inside a shoe, and may be applied mainly to bacteria floating in space inside the shoe. Of course, the sterilization emitter 48 may also be applied to bacteria on the inner surface of the shoe. There may also be an optional photocatalytic material or deodorizer (e.g., tin oxide) configured to deodorize the space when UV light is emitted toward the optional photocatalytic material. In addition, there may be an optional UV light provided at a rear of the housing 10, at a bottom of the housing 10, in the agitators 32, and/or in a support 30 or 30' that surrounds the agitators 32. Such optional UV light may be configured to turn on only when the cover 14 is closed.

Figure 4:
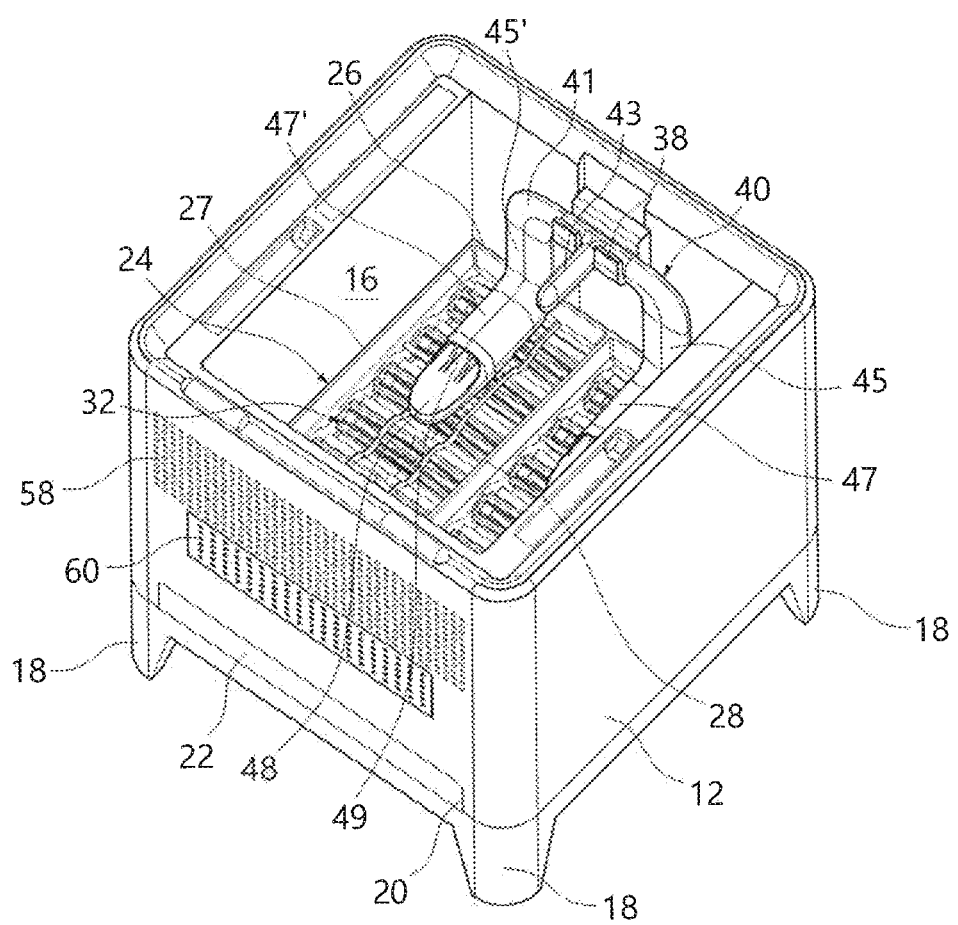
FIG. 4 is a perspective view illustrating the inside of a housing of the shoe management device illustrated in FIG. 1.

Referring to FIGS. 2-4, a first discharge part or port 49 and a second discharge part or port 49' may be provided at an upper portion or surface and the lower portion or surface, respectively, of each of the operation performance parts 47 and 47'. The first discharge part 49 and the second discharge part 49' may discharge matter needed to manage or clean shoes. For example, hot air may be discharged through the first discharge part 49, and plasma ions may be discharged through the second discharge part 49'. The first discharge part 49 may be referred to as a blower or heater, and the second discharge part 49' may be referred to as a plasma ion emitter. The hot air discharged through the first discharge part 49 may perform a drying function, and the plasma ions discharged through the second discharge part 49' may perform sterilization, disinfection, and deodorization functions. For reference, the plasma ions may also kill or inactivate bacteria inside a shoe, and be applied mainly to bacteria attached to the inner surface of the shoe. Of course, the plasma ions may also be applied to bacteria floating in space inside the shoe.

Only hot air may be simultaneously discharged through the first discharge part 49 and the second discharge part 49', or only plasma ions may be simultaneously discharged therethrough. As described above, the hot air may be discharged through the first discharge part 49, and the plasma ions may be discharged through the second discharge part 49'.

Here, the hot air and the plasma ions may be generated by the care unit 40, or hot air or plasma ions generated by components or devices located inside a rear wall of the housing 10 may be transmitted to the care unit 40 through a tube or pipe connected thereto, and may be discharged through the first discharge part 49 and/or the second discharge part 49'. The operation performance parts 47 and 47' may protrude parallel to each other, and be inserted into a pair of shoes to perform necessary functions.

For example, an inside of the operation performance parts 47 and 47' may include a heater and fan or blower to blow hot air out of the first and/or second discharge parts 49 and/or 49', and a plasma ion generator to emit plasma ions out of the first and/or second discharge parts 49 and/or 49'. An inside of the operation performance parts 47 and 47' may form a channel to guide the hot air and/or the plasma ions out of the first and second discharge parts 49 and 49'. As another example, the wall of the housing 10 may have an inner wall and an outer wall with a hollow space therebetween, and an inside of the wall of the housing 10 may include a heater and plasma ion generator, and a channel may be provided to guide ions from the plasma ion generator to the first and/or second discharge parts 49 and/or 49'. In such an example, a fan to blow hot air may be provided in the wall of the housing or inside of the operation performance parts 47 and/or 47'. An optional filter may be provided in the operation performance parts 47 and/or 47' to filter the hot air blown to heat and dry the shoes. Ends of the operation performance parts 47 and 47' may have optional sensors to sense humidity, temperature, smell, and odors, and an operation of the operation performance parts 47 and 47' may be automatically performed based on detections by the sensors.

An air flow generation part or assembly 50 may be provided inside the housing 10. The air flow generation part 50 may generate and/or allow air to flow in the inner space 16 and/or aim or blow air toward the shoes. The air flow generated by the air flow generation part 50 may remove relatively fine foreign matters such as dust on the outer surface of a shoe. Furthermore, the air flow generation part 50 may function to circulate the hot air having moisture discharged from the care unit 40.

The air flow generation part 50 may be mounted to the lower surface of the cover 14. A dividing cover 51 may form an appearance of the air flow generation part 50. The dividing cover 51 may cover components constituting the air flow generation part 50 so that the components may not be exposed. The dividing cover 51 may define a predetermined space in cooperation with the lower surface of the cover 14. A discharge or guide surface 51' may be provided on an outer surface of the dividing cover 51. The discharge surface 51' may be configured to incline toward a shoe in the inner space 16.

A fan motor 52 may be mounted in the predetermined space defined by the dividing cover 51 at a position adjacent to an introduction hole or air inlet 58 described below. The fan motor 52 may be mounted at a position adjacent to a wall constituting the inner surface of the housing 10. The fan motor 52 may rotate a fan or an impeller (e.g., a box fan) configured to suction ambient air and exhaust or blow the air to the inner space 16. The fan motor 52 and fan may be a relatively small or compact-sized fan, such as a compact high speed fan similar to the compact high speed axial fan used in some Dyson hairdryers.

The position of the fan motor 52 may be adjacent to the position of the introduction hole 5. The fan motor 52 may be provided at an inner wall of the housing 10 or between an inner wall and an outer wall of the housing 10. The fan motor 52 may alternatively be provided in a more central location inside the housing 10 or under the cover 14. An air guide duct 54 guiding an air flow may be provided in the space defined by the dividing cover 51 at a position between the fan motor 52 and discharge nozzles 56 located on the discharge surface 51'. The air guide duct 54 may have air inlet holes that are configured to align with or be provided close to the introduction hole 58 in the housing 10. An optional filter may be provided at an inner side or outer side of the air inlet holes. The air guide duct 54 may have a flow sectional area that gradually becomes larger in a direction toward the discharge surface 51' from the fan motor 52.

Two fan motors 52 and two air guide ducts 54 may be provided to provide air separately to the right shoe and the left shoe. Accordingly, when only one shoe of a pair of shoes is required to be managed, for example, when only a right shoe is required to be managed, only one fan motor 52 (e.g., a right fan motor 52) corresponding thereto may be driven to manage the shoe.

The discharge nozzles 56 may be provided on the discharge surface 51' of the dividing cover 51. The discharge nozzles 56 may be provided longitudinally in straight lines along the discharge surface 51' such that multiple nozzle holes (not shown) may be formed in the area of a straight line of each of the discharge nozzles 56. Two discharge nozzles 56 may be provided in straight lines to correspond to the right shoe and the left shoe. A diameter of each of the nozzle holes formed in the discharge nozzle 56 may be configured to be larger as a distance between the nozzle hole and the fan motor 52 increases to uniformly discharge air in the entire area of the discharge nozzle 56. Alternatively, a diameter of the nozzle holes may decrease as a distance between the nozzle hole and the fan motor 52 increases.

As another alternative, the discharge nozzles 56 may be formed of one long slit, as opposed to multiple nozzle holes, and a size or width of the slit may change based on a distance from the fan motor 52. The discharge nozzles 56 may be inclined or aimed at the shoes, may optionally move back and forth, or may have optional louvers to direct or control a flow of air. The discharge nozzles 56 may blow air toward the shoes to dust the shoes.

The introduction hole 58 may be formed through an outer surface or wall of the housing 10. The introduction hole 58 may be a flow path through which air flows to the fan motor 52 in the space defined by the dividing cover 51. The air may flow to the fan motor 52 through the flow path located in the wall in which the introduction hole 58 is formed. An inlet filter 59 may be provided at the entrance of the fan motor 52 inside of the wall so that when external air flows in, foreign matter such as dust are prevented from entering. The inlet filter 59 may be a pre filter capable of filtering dust.

A discharge opening or air outlet 60 may be formed through the wall of the housing 10. The discharge opening 60 may communicate with the inner space 16 and be a portion through which air flowing through the inner space 16 is discharged to the outside of the inner space 16. A separate discharge fan 62 and motor may be provided in the discharge opening 60, but such discharge fan 62 may be optional. The discharge fan 62 may rapidly discharge or exhaust the air in the inner space 16 to the outside. When the discharge fan 62 is used, the air of the inner space 16 can be efficiently discharged to the outside. For reference, as long as air can efficiently flow through the discharge opening 60 even without the discharge fan 62 depending on design conditions of the shoe management device, the discharge fan 62 may not be used.

An outlet filter 64 may be provided in the discharge opening 60. The outlet filter 64 may remove the dust or foreign matter of the air discharged from the inner space 16 to the outside to prevent the dust or foreign matter removed from a shoe from being transmitted to an indoor space located at the outside of the housing 10 when the shoe management device of the present disclosure is used indoors. The outlet filter 64 may have a pre filter may be used to filter dust or foreign matter and a HEPA (High-efficiency particulate air) filter used together with the pre filter to remove odor. The outlet filter 64 may have an optional deodorizer.

A fragrance or aroma sheet 66 may be provided together with the outlet filter 64. The fragrance sheet 66 may provide fragrance to air discharged through the discharge opening 60. When the fragrance sheet 66 is mounted in the discharge opening 60, a desired fragrance may be transmitted to the indoor space of the outside of the housing 10.

In addition, a component or moisture absorbent (e.g., silica) may be provided in the inner space 16 of the housing 10 to absorb moisture. Although not shown, a moisture absorbent may be provided at a side of the tray 22, and may remove moisture existing in the inner space 16. The moisture absorbent absorbing at least a predetermined amount of moisture may be replaced by taking out the tray 22 to the outside of the housing 10.

Figure 9:
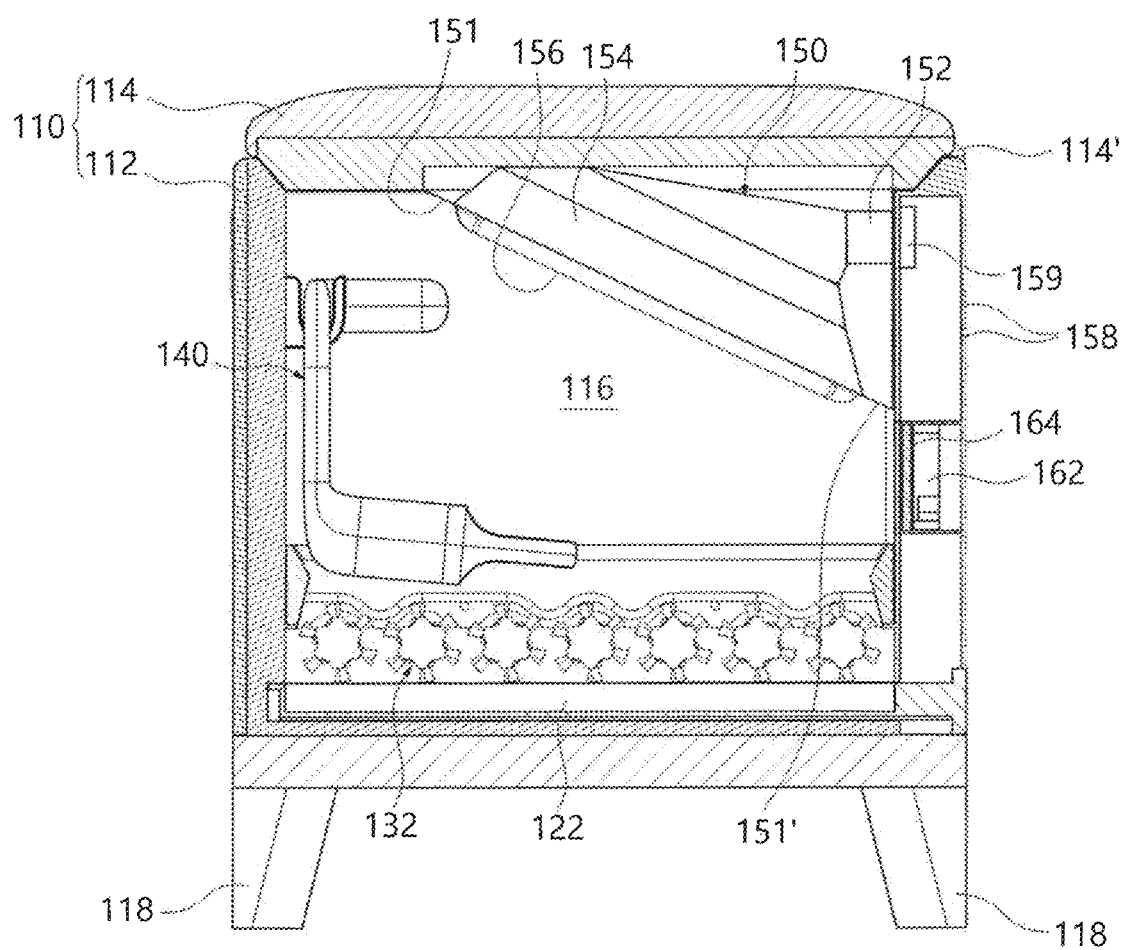
FIG. 9 is a sectional view illustrating a configuration of a shoe management device according to a another embodiment of the present disclosure.

Referring to FIG. 9, a second embodiment of the present disclosure is illustrated. The components of a shoe management device according to the embodiment illustrated in FIG. 9 will be described by assigning reference numerals between 100 and 200 to the components corresponding to the components of the device according to the embodiment illustrated in FIG. 1.

Figure 10:
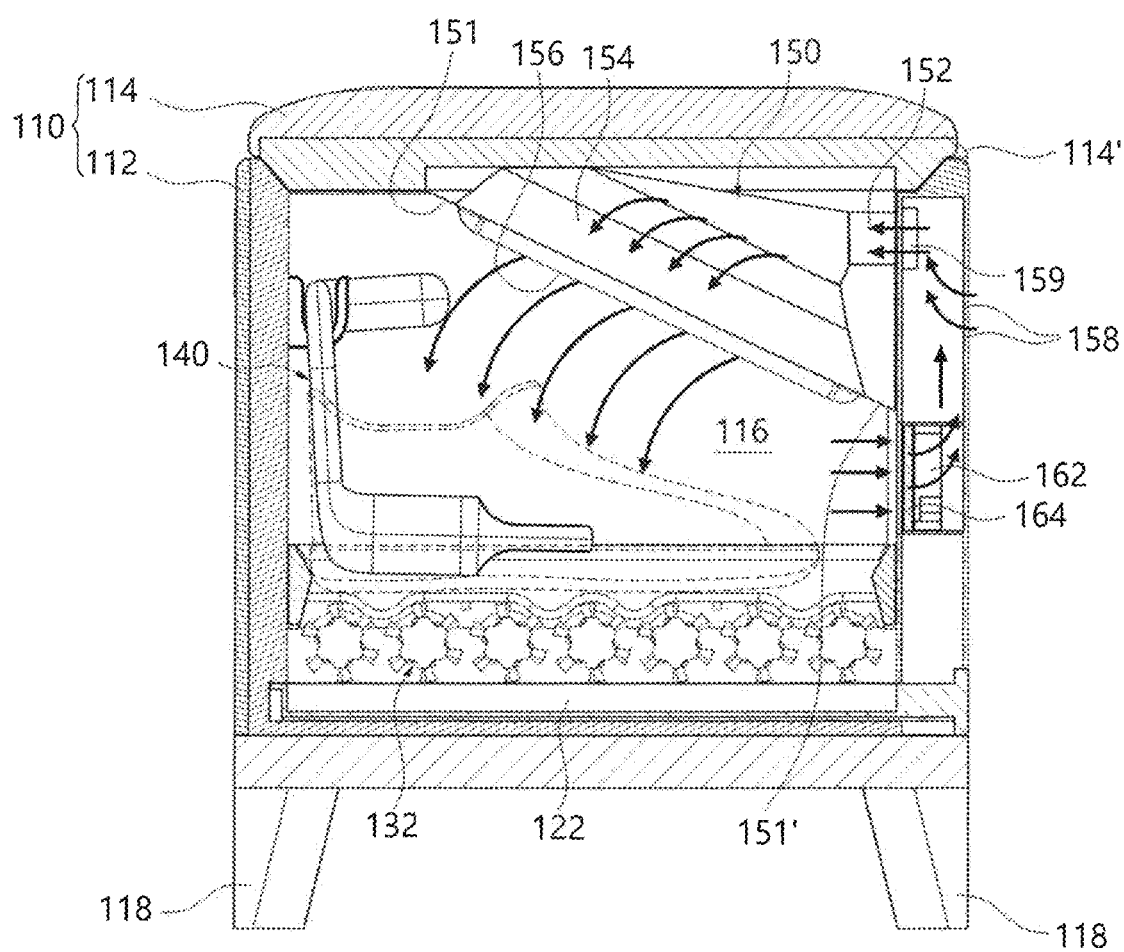
FIG. 10 is a sectional view illustrating the operation state of the shoe management device illustrated in FIG. 9.

Referring to FIGS. 9-10, air flowing through an inner space 116 of a housing body 112 may not be discharged to the outside of a housing 110, but flow through the flow path formed in the wall of the housing 110 back to an air flow generation part 150. Accordingly, there may be no separate discharge opening (which would be analogous to the discharge opening 60 open toward the outer surface of the housing in the first embodiment) in the housing 110. Of course, with the discharge opening 60 provided, a separate door may be provided in the inside or outside of the discharge opening 60, and the discharge opening 60 may be opened and/or closed as required.

A fan motor 152 of the air flow generation part 150 may be mounted at a position adjacent to an introduction hole 158, and air flow generated by the fan motor 152 may be guided along an air guide duct 154 and be discharged to the inner space 116 of the housing 110 through a discharge nozzle 156 formed on a dividing cover 151.

A circulation fan 162 may be used so that the air flowing through the inner space 116 flows to the air flow generation part 150 and again flows through the inner space 116, but such circulation fan 162 may be optional. The circulation fan 162 may be mounted in the flow path located in the wall in which the introduction hole 158 is formed, and guide air to the air flow generation part 150. A circulation filter 164 may be provided at the entrance of the circulation fan 162, and filter dust and/or odor generated in the inner space 116. As the circulation filter 164, a pre filter and/or a HEPA (High-efficiency particulate air) filter may be used. For reference, as long as an air flow is efficiently performed even without the circulation fan 162, the circulation fan 162 may not be used.

A tray 122 for foreign matter may be provided at the lower portion of the inner space 116, agitators 132 may be provided on the tray 122, and a care unit 140 inserted into the inside of a shoe may be located in the inner space 116. Reference numeral 118 refers to legs.

Figure 11:
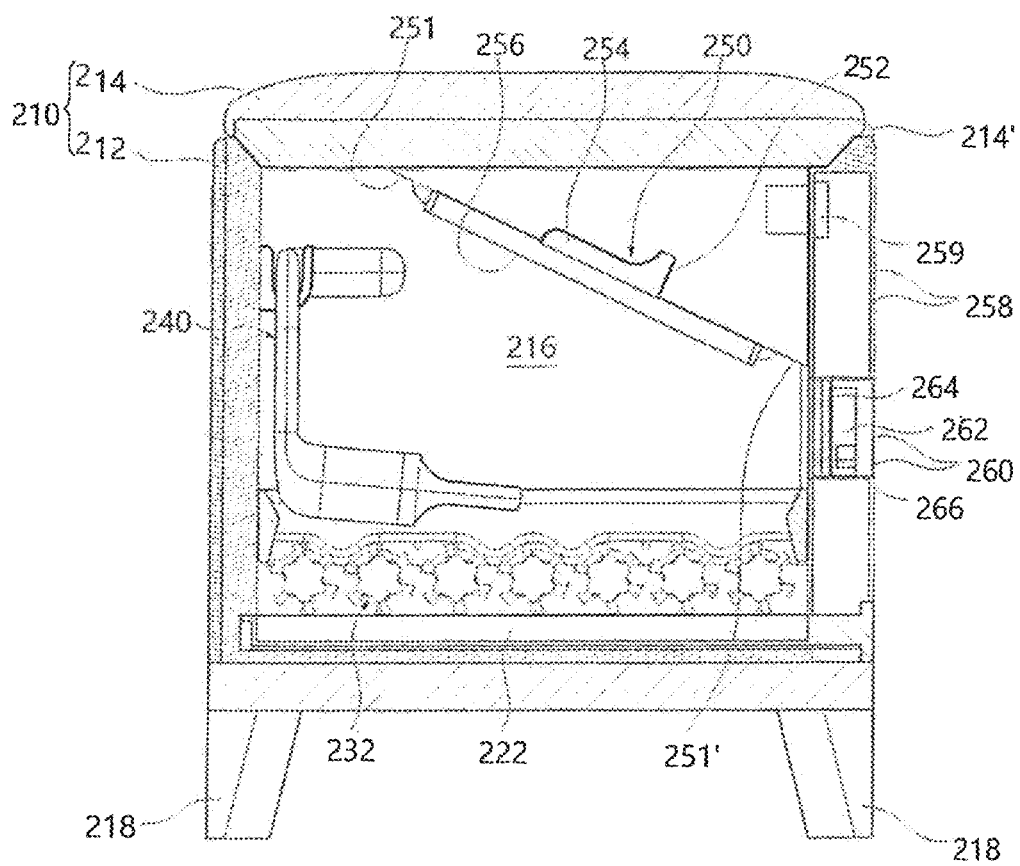
FIG. 11 is a sectional view illustrating a configuration of a shoe management device according to another embodiment of the present disclosure.
Figure 12:
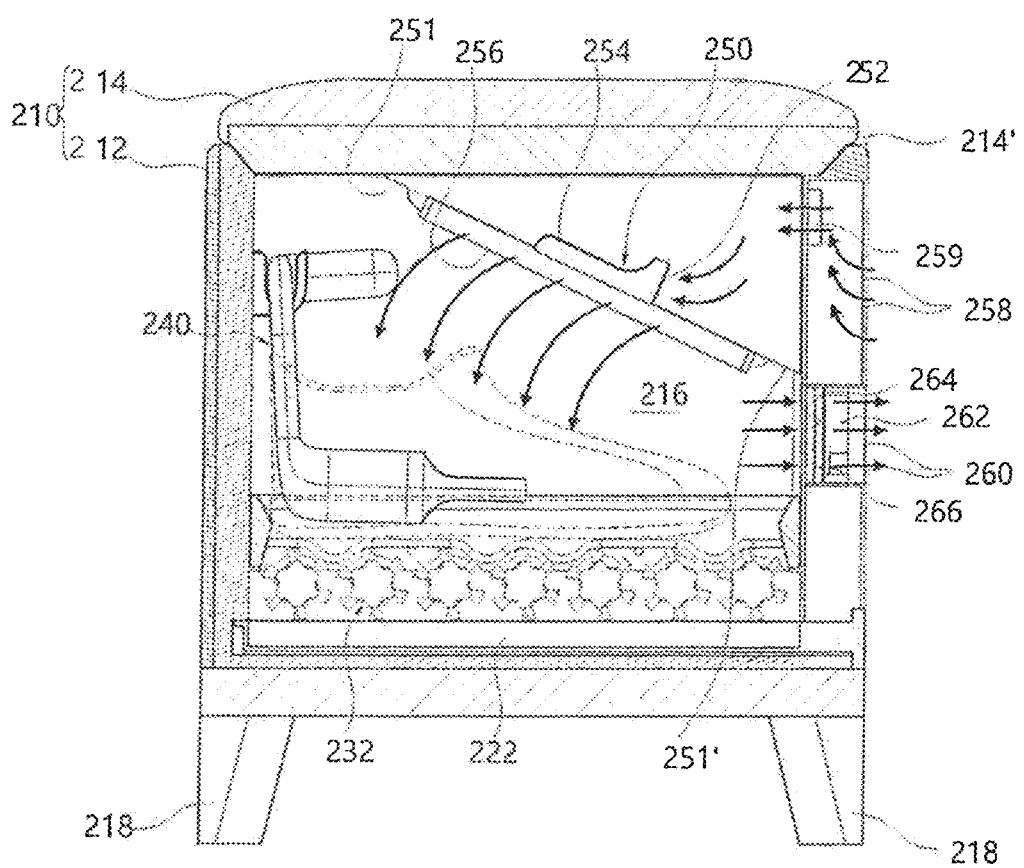
FIG. 12 is a sectional view illustrating the operation state of the shoe management device illustrated in FIG. 11.

In FIG. 11, a third embodiment of the present disclosure is illustrated. The components of the device according to the embodiment illustrated in FIG. 11 will be described by assigning reference numerals between 200 and 300 to the components corresponding to the components of the device according to the embodiment illustrated in FIG. 1. Referring to FIGS. 11-12, an introduction hole 258 through which air of the outside is introduced to an inner space 216 may be formed in an outer surface of a housing body 212, and a discharge opening 260 through which the air flowing through the inner space 216 is discharged to the outside may also be formed in an outer surface of the housing body 212.

An air flow generation part 250 may be provided for the air flow in a housing 210, and a fan motor 252 of the air flow generation part 250 may be located at an inner portion of the air flow generation part 250 located at a position relatively far from the introduction hole 258. An air flow generated by the fan motor 252 may be guided along an air guide duct 254, and lead to a discharge nozzle 256 located on a dividing cover 251.

In the embodiment, the fan motor 252 may be provided on the dividing cover 251 at a position adjacent to the discharge nozzle 256. An inlet filter 259 may be provided inside the wall of the housing 210, and air flowing through the air introduction hole 259 may flow through the inlet filter 259 before being suctioned by the fan motor 252. The air guide duct 254 guiding air to the discharge nozzle 256 located on the dividing cover 251 may extend longitudinally in a straight line to correspond to the discharge nozzle 256 formed longitudinally in a straight line. The diameter of each of nozzle holes formed in the discharge nozzle 256 may be configured to be larger as a distance between the nozzle hole and the fan motor 252 increases.

A discharge fan 262 may be provided in the discharge opening 260 formed to be open in an outer surface of the housing body 212. The discharge fan 262 may discharge the air of the inner space 216 to the outside. For reference, the discharge fan 262 may not be used depending on design conditions of the shoe management device. An outlet filter 264 may be provided at a position adjacent to the discharge fan 262. As the outlet filter 264, a pre filter filtering dust and foreign matter and/or a HEPA (High-efficiency particulate air) filter removing odor may be used. A fragrance sheet 266 may also be provided at a position adjacent to the discharge opening 260. The fragrance sheet 266 allows fragrance to be mixed with air discharged through the discharge opening 260.

The tray 222 may be provided at the lower portion of the inner space 216, agitators 232 may be provided on the tray 222 for foreign matter, and a care unit 240 inserted into a shoe may be located in the inner space 216. Reference numeral 218 refers to legs.

Figure 13:
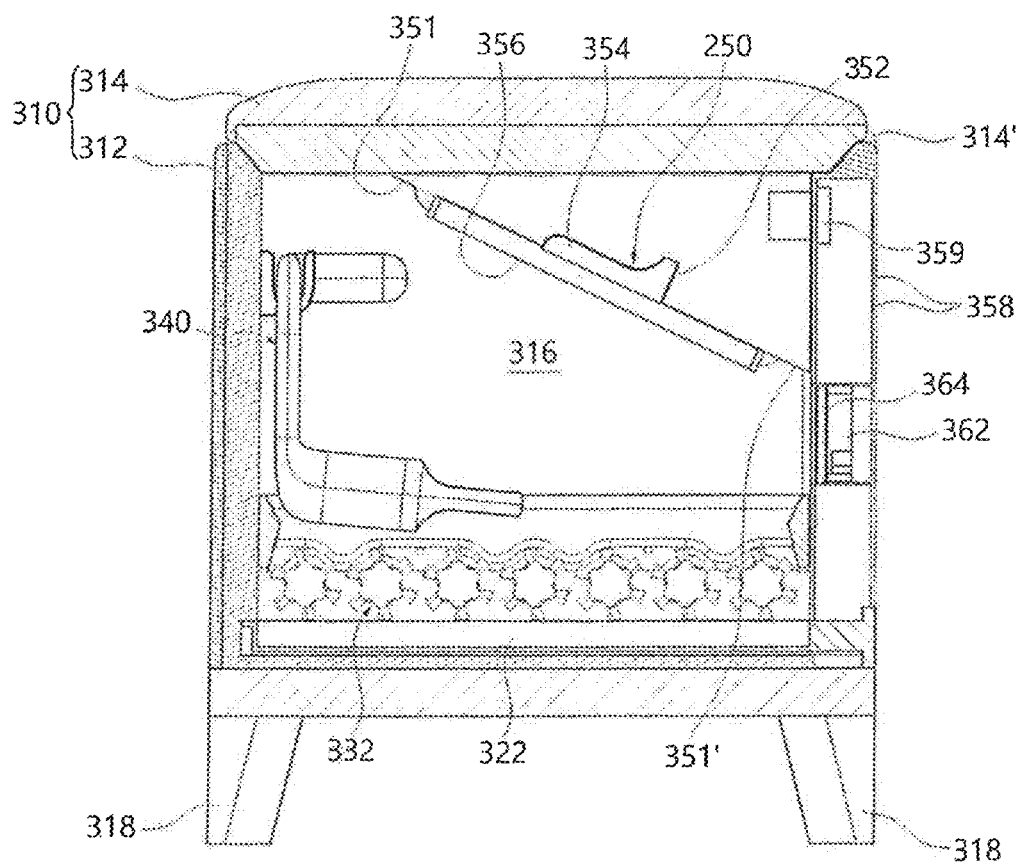
FIG. 13 is a sectional view illustrating a configuration of a shoe management device according to another embodiment of the present disclosure.
Figure 14:
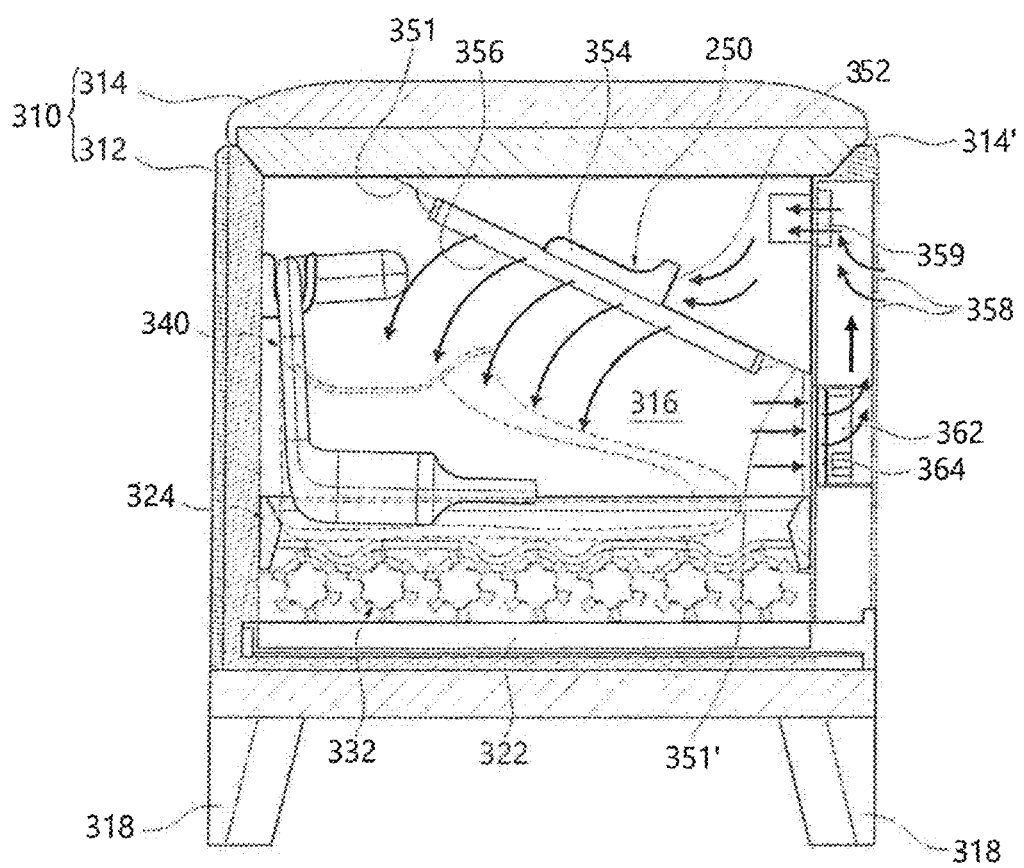
FIG. 14 is a sectional view illustrating the operation state of the shoe management device illustrated in FIG. 13.

In FIG. 13, a fourth embodiment of the present disclosure is illustrated. In the embodiment, the components of a shoe management device according to the embodiment illustrated in FIG. 13 will be described by assigning reference numerals between 300 and 400 to the components corresponding to the components of the device according to the embodiment illustrated in FIG. 1. Referring to FIGS. 13-14, an introduction hole 358 through which air of the outside is introduced to an inner space 316 may be provided at an outer surface of a housing body 312. The air flowing through the inner space 316 may be transmitted to an air flow generation part 350, and recirculate through the inner space 316.

The air flow generation part 350 may be provided for the air flow in the housing 310, and a fan motor 352 of the air flow generation part 350 may be located at an inner portion of the air flow generation part 350 relatively far away from the introduction hole 358, similar to the embodiment of FIGS. 11-12. The air flow generated by the fan motor 352 may be guided along an air guide duct 354, and lead to a discharge nozzle 356 on a dividing cover 351. In the embodiment, the fan motor 352 may be provided on the dividing cover 351 located at a position adjacent to the discharge nozzle 356. The air guide duct 354 guiding air to the discharge nozzle 356 located on the dividing cover 351 may extend longitudinally in one direction to correspond to the discharge nozzle 356 formed longitudinally in a straight line. The diameter of each of nozzle holes formed in the discharge nozzle 356 may be configured to be larger as a distance between the nozzle hole and the fan motor 352 increases. An inlet filter 359 may be provided at the inner surface of wall of the housing 310.

A circulation fan 362 may be provided so that the air flowing through the inner space 316 is transmitted to the air flow generation part 350 and again flows through the inner space 316. The circulation fan 362 may be provided in the flow path formed in the wall in which the introduction hole 358 is formed and flow air to the air flow generation part 350. If air circulation is efficiently performed even without the circulation fan 362, the circulation fan 362 may not be used.

The circulation filter 364 may be provided at the entrance of the circulation fan 362 and filter dust generated in the inner space 316. As the circulation filter 364, a pre filter and/or a HEPA (High-efficiency particulate air) filter may be used.

A tray 322 for foreign matter may be provided at the lower portion of the inner space 316, agitators 332 may be provided on the tray 322, and a care unit 340 inserted into a shoe may be located in the inner space 316. Reference numeral 318 refers to legs.

Figure 15:
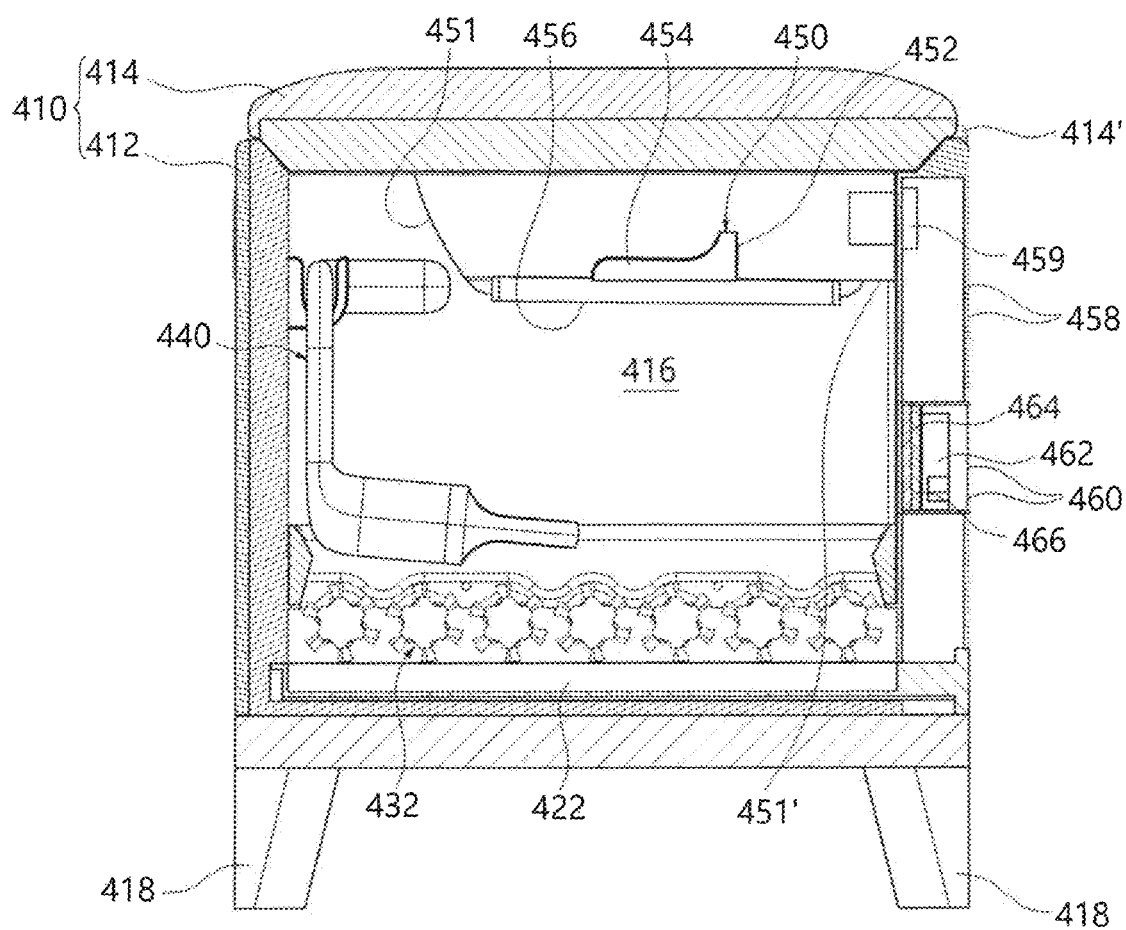
FIG. 15 is a sectional view illustrating a configuration of a shoe management device according to another embodiment of the present disclosure.
Figure 16:
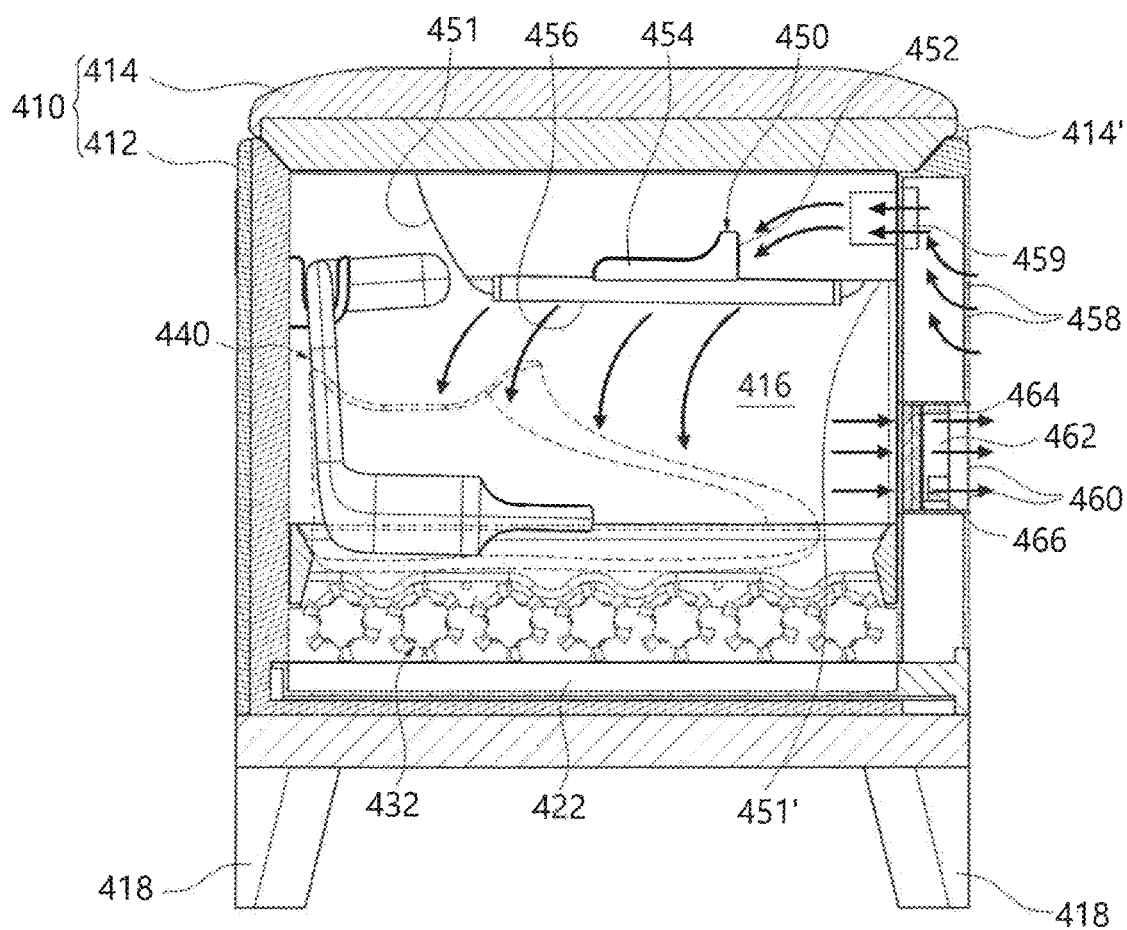
FIG. 16 a sectional view illustrating the operation state of the shoe management device illustrated in FIG. 15.

In FIG. 15, a fifth embodiment of the present disclosure is illustrated. In the embodiment, the components of a shoe management device according to the embodiment illustrated in FIG. 15 will be described by assigning reference numerals between 400 and 500 to the components corresponding to the components of the device according to the embodiment illustrated in FIG. 1. Referring to FIGS. 15-16, an introduction hole 458 through which air of the outside is introduced to an inner space 416 may be formed in an outer surface of a housing body 412, and a discharge opening 460 through which the air flowing through the inner space 416 is discharged to the outside may also be formed in an outer surface of the housing body 412.

In the embodiment, an air flow generation part 450 may be provided for the air flow inside the housing 410, and a discharge surface 451' of a dividing cover 451 of the appearance of the air flow generation part 450 may directly face agitators 432 located under the discharge surface 451'. That is, the discharge surface 451' may not be inclined as in the previous embodiments, but be parallel to the bottom surface of the housing 410. Accordingly, air discharged through a discharge nozzle 456 of the discharge surface 451' may flow directly downward toward a shoe without inclining toward the shoe.

In the embodiment, a fan motor 452 of the air flow generation part 450 may be located at an inner portion of the air flow generation part 450 relatively far from the introduction hole 458, but the fan motor 452 may alternatively be located at a position adjacent to the introduction hole 458 closer to an inlet filter 459.

In the embodiment, a discharge fan 462 may be provided in the discharge opening 460 formed to be open in an outer surface of the housing body 412. The discharge fan 462 may discharge the air of the inner space 416 to the outside. For reference, as long as the air flow through the discharge opening 460 is performed even without the discharge fan 462, the discharge fan 462 may not be used.

An outlet filter 464 may be provided at a position adjacent to the discharge fan 462. As the outlet filter 464, a pre filter filtering dust and foreign matter and/or HEPA (High-efficiency particulate air) filter removing odor may be used. A fragrance sheet 466 may also be provided at a position adjacent to the discharge opening 460. The fragrance sheet 466 may allow fragrance to be mixed with the air discharged through the discharge opening 460.

As an alternative, the discharge opening 460 may be omitted or configured to be closed, and the discharge fan 462 may be a circulation fan so that air circulating in the inner space 416 may be transmitted to the air flow generation part 450 and recirculate through the inner space 416.

Hereinafter, the operation of the shoe management device having the configuration described above according the embodiments of the present disclosure will be described in detail.

First, the operation of the shoe management device illustrated in FIG. 1 with reference to FIG. 8 will be described.

A user opens the cover 14, and inserts shoes into the inner space 16 to be provided on the first support member 30 and the second support member 30' of the internal frame 24. The operation performance parts 47 and 47' of the care unit 40 may be inserted into the right shoe and the left shoe located in the inner space 16, respectively. An installation or mounting position of the care unit 40 may be changed by adjusting the height of the holding column 36 according to the height of each of the shoes. Accordingly, the operation performance parts 47 and 47' of the care unit 40 may be accurately and/or conveniently located inside the shoes.

Figure 8:
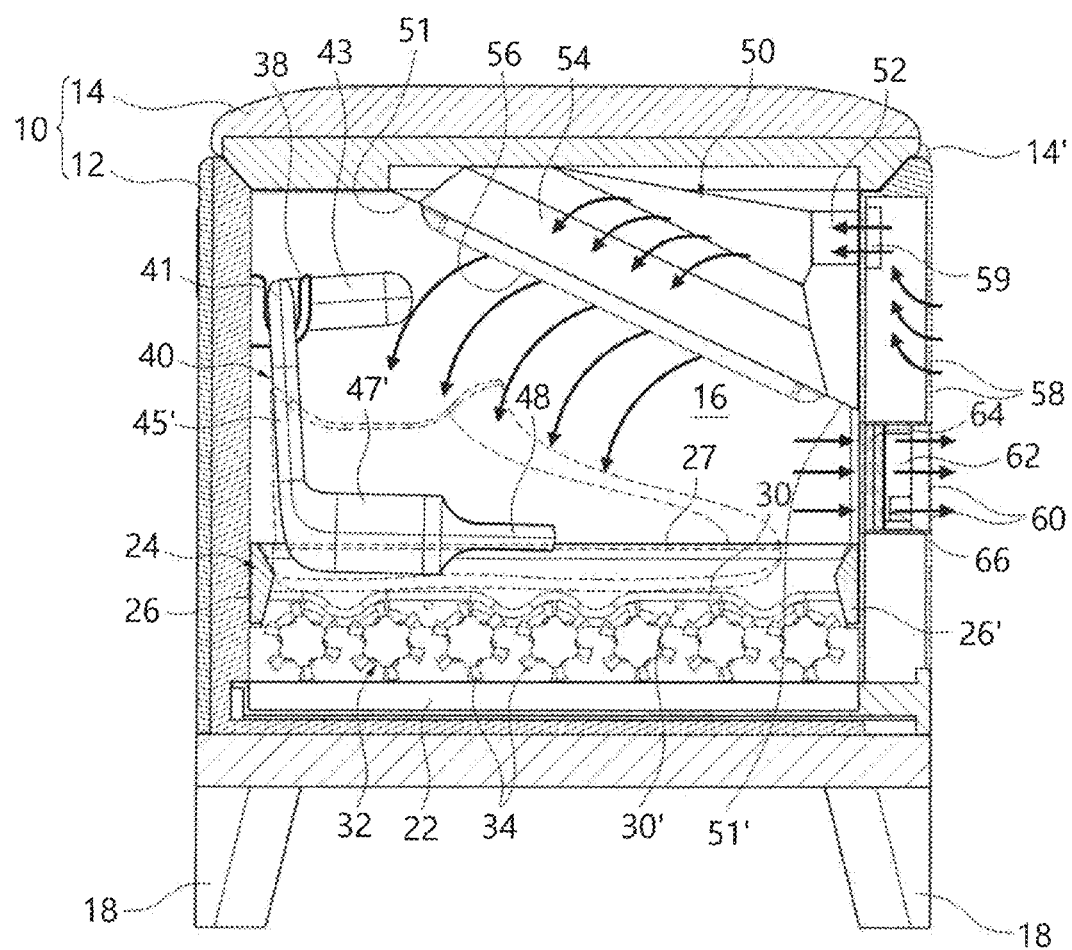
FIG. 8 is a sectional view illustrating an operation state of the shoe management device illustrated in FIG. 1.

In such a state, when the cover 14 is closed, the inner space 16 may be isolated from the outside, and the discharge surface 51', which is a surface of the dividing cover 51 of the air flow generation part 50, may face the upper portion of the shoe as illustrated in FIG. 8. Accordingly, the discharge nozzles 56 located on the discharge surface 51' may be located at positions corresponding to the left shoe and the right shoe. For reference, when the cover 14 is closed, the closing of the cover 14 may be detected, and the operation of the shoe management device may be performed.

The operation of the shoe management device may be divided into three major operations. There are the operations of the agitators 32, the care unit 40, and the air flow generation part 50. First, as for the operation of the agitators 32, due to the rotations of the agitators 32, the removal ribs 34 may scrape or brush the lower surface of a shoe, and remove foreign matter such as dirt or dust. The agitators 32 adjacent to each other may remove foreign matter on the lower surface of the shoe while rotating in directions opposite to each other to prevent or reduce forward and backward movement of the shoe. The care unit 40 may restrict upward movement of the shoe toward the upper portion of the inner space 16. Accordingly, while the shoe may be located on the internal frame 24, foreign matter on the lower surface of the shoe may be efficiently removed.

While the agitators 32 operate, foreign matter removed from a shoe may fall by weight and be transmitted onto the tray 22. Much foreign matter may fall on the tray 22. After being used for a predetermined time, the tray 22 may be taken out to the outside of the housing 10 so that the foreign matter is removed and discarded therefrom, and may be inserted back into the inner space 16 through the tray opening 20.

In addition, foreign matter or dirt on the lower end portions of side surfaces of the shoe as well as on the lower surface of the shoe may be removed by the operations of the agitators 32. This is because each of the removal ribs 32 is made of an elastic material and an end portion of a side of the removal rib 32 can reach a lower end portion of a side surface of the shoe. Alternatively or in addition thereto, the removal ribs 32 may be or include bristles to brush dirt from crevices formed in a bottom of the shoe. For example, some of the removal ribs 32 may be elastic or deformable blades, and other removal ribs 32 may be a set of bristles. The removal ribs 34 may have a predetermined inclination or curvature, and be formed with indentations or grooves configured to receive the first and/or second supporting members 30 and 30' so that at least a portion of the removal ribs 34 protrude upward to contact a bottom of the shoes.

Second, the moisture of the inside of the shoe may be removed, and/or sterilization and deodorization may be performed by the operation of the care unit 40. When hot air is discharged through the first discharge part 49 with the operation performance part 47 of the care unit 40 located inside the shoe, the hot air may be transmitted to the inside of the shoe and dry the inside thereof. The hot air having moisture therein may flow to the inner space 16 outside of the shoe, and flow therein together with the air flow generated by the air flow generation part 150 in the inner space 16.

The sterilization emitter 48 of the care unit 40 may perform sterilization inside the shoe. The sterilization emitter 48 may make the inside of the shoe more hygienic by killing germs such as bacteria living inside the shoe, or by reducing the activity thereof. The sterilization emitter 48 may be located at the front end of the operation performance part 47, and enter deeper inside the shoe, whereby sterilization and deodorization may be performed up to the front end of the inside of the shoe. The sterilization emitter 48 may be used mainly to remove bacteria floating in the inner space of the shoe.

Next, plasma ions may be discharged through the second discharge part 49' located in the operation performance part 47 of the care unit 40, whereby sterilization and deodorization of the inside of the shoe may be performed. Particularly, the plasma ions may flow up to a position where the sterilization emitter 48 may not reach, and sterilize and deodorize every corner of the inside of the shoe. For reference, the plasma ions may be used mainly to remove bacteria attached to the inner surface of the shoe.

In addition, the hot air and the plasma ions have been described to be discharged through the first discharge part 49 and the second discharge part 49', respectively, but the hot air may be discharged simultaneously through the first discharge part 49 and the second discharge part 49', and later the plasma ions may be discharged simultaneously through the first discharge part 49 and the second discharge part 49'.

Third, due to the operation of the air flow generation part 50, foreign matter such as dust on the surface of a shoe may be removed. The foreign matter such as dust removed by the air flow generation part 50 may be finer than foreign matter removed by the agitators 32. The flow of air may be generated by the fan motor 52 of the air flow generation part 50, and the air may be discharged through the discharge nozzle 56 and hit the outer surface of a shoe. Relatively large foreign matter may be removed from and fall from the shoe and be transmitted to the tray 22 by the agitators 32, whereas fine dust which can flow along with the air flow may be removed by the air flow generated by the air flow generation part 50.

The air discharged to the shoe through the discharge nozzle 56 may be discharged through the discharge opening 60 to the outside of the housing 10 as illustrated with arrows in FIG. 8. In this case, while the air passes through the outlet filter 64, foreign matter contained in the air may be removed, and odor may also be removed. With fragrance mixed with the air by the fragrance sheet 66 while the air passes through the discharge opening 60, the air may be discharged through the discharge opening 60 by the discharge fan 62.

In addition, when a moisture absorbent is arranged at a side inside the housing 10, moisture in the shoe may be absorbed and removed by the moisture absorbent. Accordingly, the moisture may not be transmitted to the outside through the discharge opening 60, whereby the environment of space in which the device of the present disclosure is located may be maintained pleasant.

Here, the air flow generated by the fan motor 52 of the air flow generation part 50 will be described briefly. When the fan motor 52 is operated, the air of the outside may be introduced to the inner space through the introduction hole 58. When the air flows to the fan motor 52, the air may pass through the inlet filter 59, and foreign matter of the air may be removed from the air. The air flow generated by the fan motor 52 may be guided along the air guide duct 54, and be discharged through the discharge nozzle 56. The diameter of each of the nozzle holes of the discharge nozzle 56 may be preset or predetermined in consideration of the distance between the nozzle hole and the fan motor 52 such that the air may be almost uniformly discharged in the entire area of the discharge nozzle 56.

Accordingly, in the present disclosure, foreign matter such as dust may be removed, and dehumidification, deodorization, and sterilization may be performed by the operations of the agitator 32, the care unit 40, and the air flow generation part 50 inside the inner space 16 of the housing 10, whereby a shoe can be more hygienically managed.

Next, the embodiment illustrated in FIG. 9 will be described with reference to FIG. 10.

In the embodiment illustrated in FIG. 9, the operations of the agitators 132 and the care unit 140 are the same as the operations of the agitators 32 and the care unit 40 in the embodiment of FIG. 8, so the air flow generated by the air flow generation part 150 will be described below.

The air flow generated by the fan motor 152 of the air flow generation part 150 may be guided by the air guide duct 154 and be transmitted to the discharge nozzle 156. The air discharged from the discharge nozzle 156 may be transmitted to the surface of a shoe in the inner space 116, and carry dust on the surface of the shoe and absorb moisture thereon to circulate together therewith. The air flow may not be transmitted from the inner space 116 to the outside, and may be transmitted back to the fan motor 152 by the circulation fan 162 located in the flow path formed in the wall of the housing 110 as illustrated in FIG. 10. In this case, foreign matter and/or odor in the air may be removed by the circulation filter 164.

In addition, when the air flows to the fan motor 152, foreign matter may be removed again by an inlet filter 159. The air passing through the inlet filter 159 may include external air introduced through the introduction hole 158 as well as air circulating in the inner space 116. The air may be purified or filtered while passing through the inlet filter 159, may be suctioned or pulled by the fan motor 152, may be guided along the air guide duct 154, and may be discharged to the inner space 116 through the discharge nozzle 156, whereby as described above, moisture and foreign matters of the surface of a shoe may be removed.

Next, the operation of the shoe management device according to the embodiment illustrated in FIG. 11 will be described with reference to FIG. 12. Here, the operations of the agitators 232 and the care unit 240 are the same as the operations of the agitators 32 and the care unit 40 of the embodiment of FIG. 8, so the description thereof will be omitted for convenience.

In the embodiment, due to the operation of the air flow generation part 250, foreign matter such as dust and dirt on the surface of a shoe may be removed. The foreign matter removed by the air flow generation part 250 may be finer than foreign matter removed by the agitators 232. Here, the air flow may be generated by the fan motor 252, and the air may be discharged through the discharge nozzle 56 and hit the outer surface of a shoe. Due to such action, relatively large foreign matters may be removed from and fall from the shoe and be transmitted onto the tray 222 by the agitators 232, whereas fine dust which may flow along with the air flow may be removed by the air flow generated by the air flow generation part 250.

The air discharged to the shoe through the discharge nozzle 256 may be discharged through the discharge opening 260 to the outside of the housing 210 as illustrated with arrows in FIG. 12. In this case, while the air passes through the outlet filter 264, foreign matter contained in the air may be removed, and odor may also be removed. With fragrance mixed with the air by the fragrance sheet 266 while the air passes through the discharge opening 260, the air may be discharged through the discharge opening 260 by the discharge fan 262.

Although the air of the inner space 216 may be discharged to the outside of the housing 210, the discharged or exhausted air may not include moisture, dust, and odor. Fragrance provided by the fragrance sheet 266 may be transmitted to the indoor space, andy the indoor space can be maintained pleasant.

Next, the operation of the shoe management device according to the embodiment illustrated in FIG. 13 will be described with reference to FIG. 14.

In the embodiment, the operations of the agitators 332 and the care unit 340 are the same as the operations of the agitators 32 and the care unit 40 of the embodiment of FIG. 8, so the description thereof will be omitted for convenience.

An air flow generated by the fan motor 352 of the air flow generation part 350 may be guided by the air guide duct 354 and be transmitted to the discharge nozzle 356. The air discharged through the discharge nozzle 356 may be transmitted to the surface of the shoe in the inner space 316, carry dust on the surface of the shoe, and absorb moisture thereon to circulate together therewith. The air flow may not be transmitted from the inner space 316 to the outside, and instead be transmitted back to the fan motor 352 by the circulation fan 362 located in the flow path formed in the wall of the housing 310 as illustrated in FIG. 14. In this case, foreign matter and/or odor in the air may be removed by the circulation filter 364.

In addition, when the air flows to the fan motor 352, foreign matters may be removed again by an inlet filter 359. The air passing through the inlet filter 359 may include external air introduced through the introduction hole 358 as well as air circulating in the inner space 316. The air may be purified or filtered while passing through the inlet filter 359, may be pulled or suctioned by the fan motor 352, may be guided along the air guide duct 354, and may be discharged to the inner space 316 through the discharge nozzle 356, whereby as described above, moisture and foreign matter of the surface of a shoe may be removed.

Next, the operation of the shoe management device according to the embodiment illustrated in FIG. 15 will be described with reference to FIG. 16. In the embodiment, the discharge surface 451' of the dividing cover 451 may be configured to have no inclination and be parallel to the agitators 432 on the bottom of the housing 410. Accordingly, air discharged through the discharge nozzle 456 located on the discharge surface 451' may flow vertically downward in the inner space 416, and remove dust and foreign matter on the surface of a shoe. Large foreign matter may fall on a tray 422, whereas, due to the operation of the discharge fan 462, fine foreign matter may flow out of the inner space 416 together with the air.

In this process, the outlet filter 464 may filter the foreign matter in the air before the air flows to the outside of the housing 410, and when the fragrance sheet 466 is used, air mixed with fragrance may be transmitted to the indoor space.

This application is related to co-pending U.S. application Ser. No. 17/073,511 filed on Oct. 19, 2020, the entire contents of which are incorporated by reference herein.

Embodiments disclosed herein may be implemented as a shoe management device comprising a housing having an inner space configured to store at least a pair of shoes, an air flow generator provided in the inner space and configured to blow air toward the shoes, and a shoe dryer provided in the inner space and configured to be inserted into each of the pair of shoes. The shoe dryer may include ultraviolet (UV) light to sterilize the shoes and plasma ions to disinfect the shoes.

The shoe dryer may include a body coupled to a rear of the housing and at least a pair of forward extensions protruding forward and configured to be inserted into the pair of shoes, respectively. Each of the forward extensions may have a UV light emitter and at least one discharge channel configured to discharge at least one of plasma ions or hot hair.

The UV light emitter may be provided at a front end of the forward extension. The at least one discharge channel may include a first discharge channel provided on an upper surface of the forward extension and a second discharge channel provided on a lower surface of the forward extension. The first and second discharge channels may be configured to discharge hot air and plasma ions simultaneously or sequentially.

The body of the shoe dryer may be U-shaped so as to have downward extensions extending downward. The forward extensions may extend forward from the downward extensions. The body further may include a handle protruding forward from a center of an upper portion.

A holding column may be mounted to the rear of the housing. The body of the shoe dryer may be hung on the holding column. The holding column may be configured to have an adjustable height such that a height of the shoe dryer may be adjusted.

A plurality of agitators may be provided at a bottom of the inner space and configured to rotate under the shoes. Each of the agitators may have a plurality of ribs provided at predetermined angular intervals on an outer circumferential surface. The ribs may be made of a deformable material.

A tray may be provided under the agitators to collect foreign matter falling from the shoes. The agitators may be provided in at least a pair of columns to correspond to the pair of shoes. The tray may be configured to be inserted into and withdrawn from the housing to discard the collected foreign matter.

The ribs may extend between opposite ends of each of the agitators. Rach of ribs may have a predetermined curvature.

An internal frame may be provided in the inner space to surround the agitators. A first support may extend between opposite sides of the internal frame. A second support may extend between opposite ends of the internal frame to intersect with the first support. The first and second supports may be configured to support the shoes.

The agitators may be provided in at least a pair of columns to correspond to the pair of shoes. Curved portions may be formed in the first support, which may extend in a longitudinal direction of the columns in which the agitators are arranged. Each of the curved portions may be provided between adjacent agitators in a same column.

Curved grooves may be formed in a bottom portion of the internal frame. The curved grooves may be configured to avoid interference with the agitators. Adjacent agitators may be configured to rotate in opposite directions so not to move the shoes in a single direction.

Embodiments disclosed herein may be implemented as a shoe management device comprising a housing having an inner space configured to store a plurality of shoes, a shoe dryer provided in the inner space and having a plurality of forward extensions configured to be inserted into the plurality of shoes, respectively, and to emit at least one of ultraviolet (UV) light or plasma ions to an inside of the shoes, and a plurality of agitators provided at a bottom of the inner space and configured to remove foreign matter from the shoes.

The forward extensions may include a UV light emitter provided at a front end, a first discharge port provided on an upper surface, and a second discharge port provided on a lower surface. The first and second discharge ports may be configured to emit hot air and plasma ions simultaneously or sequentially.

The shoe dryer may comprise a body, the plurality of forward extensions protruding forward from the body, a plurality of downward extensions extending downward from the body, and a handle protruding forward from a center of the body.

The agitators may be arranged in a plurality of columns to correspond to the plurality of shoes. A tray may be provided under the agitators to collect foreign matter. The tray may be configured to be inserted into and withdrawn from the housing.

An internal frame may be provided in the inner space to surround the agitators. A first support may be provided on the internal frame and extend in a forward-rearward direction. A second support may be provided on the internal frame and extend in a left-right direction to intersect with the first support. The first and second supports may be configured to support the plurality of shoes. A blower may be configured to blow air toward the shoes to remove foreign matter from the shoes.

In the above, although all components constituting the shoe management device of the present disclosure are described as being coupled to each other into one to be operated, the present disclosure may be not necessarily limited to these embodiments. That is, within the scope of the present disclosure, all of its components may operate by being selectively coupled to each other into at least one. In addition, the terms "include", "constitute", or "have" as described above mean that the corresponding components may be included, unless otherwise stated, and it should be interpreted that other components may be further included, not excluded. All terms, including technical or scientific terms, have the same meaning as generally understood by those skilled in the art to which the present disclosure belongs, unless otherwise defined. Commonly used terms, such as those defined in the dictionary, should be interpreted as being consistent with the contextual meaning of the related art, and should not be interpreted as an ideal or excessively formal meaning unless explicitly defined in the present disclosure.

The above description is merely illustrative of the technical idea of the present disclosure, and those having ordinary skills in the technical field to which the present disclosure belongs can make various modifications and variations without departing from the essential characteristics of the present disclosure. Accordingly, the embodiments disclosed in the present disclosure are not intended to limit the technical idea of the present disclosure, but to explain the technical spirit, and the scope of the technical idea of the present disclosure is not limited to these embodiments. The scope of protection of the present disclosure should be interpreted by the claims below, and all technical ideas within the scope equivalent thereto should be interpreted as being included in the scope of the present disclosure.

For reference, in the illustrated embodiments, the fan motor 52 may be provided in the housing 10 to move air in the inner space 16 of the housing 10. However, instead of the fan motor 52, the circulation fan may be provided in the flow path located in the wall of the housing 10 so as to allow the air flow to be performed in the entirety of the inner space of the housing 10. This case may be applied to the configuration having no discharge opening among the various embodiments described above, and the air pressed or moved by the circulation fan may be discharged through the discharge nozzle to the inner space 16 so that air flowing through the inner space 16 recirculates in the inner space 16.

Accordingly, the present disclosure has been made keeping in mind the above problems occurring in the related art, and the present disclosure is intended to propose a shoe management device, wherein foreign matter such as dirt on the surface of a shoe can be removed, and temperature, humidity, and odor inside the shoe can be optimized.

In addition, the present disclosure is intended to propose a shoe management device wherein fine dust and relatively large foreign matters on the shoe are automatically removed. A shoe may be managed with the shoe placed in a space separated from the outside. An inside of a shoe may be sterilized and disinfected by using plasma ions.

In order to achieve the above objectives, according to one aspect of the present disclosure, a shoe management device may include an air flow generation part provided inside a housing having an inner space. Air may be discharged to a shoe arranged in the inner space and allow foreign matters to be removed from the shoe so as to hygienically manage the outer portion of the shoe.

A care unit inserted into the shoe may be mounted in the housing having the inner space and may sterilize the shoe. According to such a present disclosure, the inside of the shoe may be managed hygienically. The care unit may supply plasma ions into a shoe so germs and odor inside the shoe may be removed.

Operation performance parts may be provided in the care unit. Each of the operation performance parts may be located inside a shoe and allow the state of the inside of the shoe to be pleasant. Each operation performance part may include a sterilization emitter and a discharge part, so moisture, germs, and odor inside the shoe may be removed.

According to the present disclosure, the sterilization emitter may be provided on the front end of the operation performance part, and a first discharge part and a second discharge part may be provided on the upper surface and lower surface of the operation performance part. The first discharge part and the second discharge part may discharge at least any one of hot air and plasma ions simultaneously or sequentially. Accordingly, moisture, germs, and odor inside a shoe may be effectively removed by the operation performance part of the care unit.

According to the present disclosure, the care unit may include a body part, extension parts extending downward from the opposite ends of the body part, the operation performance parts protruding forward from the extension parts, and a handle protruding from the center of the body part in a direction parallel to the operation performance parts. The body part may have an upside down U-shape. The care unit having such a configuration may be easy to handle and allow the management of the shoe to be more efficiently performed in the inner space.

The care unit may be provided by being hung on a holding column mounted in the inner space, and the height of the holding column may be adjusted. Accordingly, the installation height of the care unit may be adjusted and shoes having various heights may be managed.

Agitators may be provided on the bottom of the inner space of the housing. Each of the agitators may have multiple elastically transformable removal ribs provided at predetermined angular intervals on an outer surface thereof, so foreign matter and dust on the surface of a shoe may be more efficiently removed by the removal ribs.

The agitators may be provided in multiple columns. A tray for foreign matter on which the foreign matter removed by the agitators fall may be provided under the agitators, and may be inserted into and taken out from the housing as a drawer. Accordingly, relatively large foreign matter on the surface of a shoe may be easily removed therefrom and be transmitted to the tray.

The removal ribs may extend toward opposite end portions of each of the agitato, and be configured as a curved line having a predetermined curve. The removal ribs may be configured in the shape of the curved line and provide a predetermined amount of pressure to the surface of the shoe while the removal ribs move with being in close contact with the surface of the shoe, so foreign matter on the shoe may be more efficiently removed.

An internal frame may be provided in the inner space by surrounding the agitators. A first support member and a second support member may be mounted to the internal frame and support a shoe on the agitators. Accordingly, the shoe may not be seated directly on the agitators, but may be seated on the first support member and the second support member. In this state, foreign matters may be more efficiently removed by the agitators.

Curved portions may be formed in the first support member extending in a direction of a column in which each of the agitators is arranged, each of the curved portions being located between the agitators, so the removal ribs of the agitator may be more in close contact with the surface of a shoe. Curved grooves may be formed in lower ends of side end members constituting opposite sides of the internal frame, the curved grooves being configured to avoid interference of the side end members with the agitators. A degree of contact between a shoe and the agitators may become closer.

The inner space in which a shoe is located may be provided in the housing, and the agitators may be located on the bottom of the inner space so foreign matter on the shoe may be removed. In such a present disclosure, the inside and outside of the shoe may be managed more hygienically.

The sterilization emitter may be provided in the operation performance part provided in the care unit. The first discharge part and the second discharge part may be provided on the upper surface and lower surface of the operation performance part to perform drying and sterilization. The first discharge part and the second discharge part may discharge at least any one of the hot air and the plasma ions simultaneously or sequentially. Accordingly, moisture, germs, and odor may be effectively removed by the operation performance part of the care unit.

According to the present disclosure, the care unit may include the body part, the extension parts extending downward from the opposite ends of the body part, the operation performance parts protruding forward from the extension parts, and the handle protruding from the center of the body part in the direction parallel to the operation performance parts. The care unit having such a configuration may be easy to handle and allow the management of the shoe to be more efficiently performed in the inner space.

The agitators may be provided in multiple columns. The tray on which the foreign matter removed by the agitators falls may be provided under the agitators and may be inserted into and taken out from the housing as a drawer. Relatively large foreign matter on the surface of a shoe may be easily removed therefrom and be transmitted to the tray.

The internal frame may be provided in the inner space by surrounding the agitators. The first support member and the second support member may be mounted to the internal frame and support a shoe on the agitators. The shoe may not be seated directly on the agitators, but may be seated on the first support member and the second support member. In this state, foreign matter may be more efficiently removed by the agitators.

The embodiments disclosed herein have at least one of the following effects.

In the shoe management device, at least the care unit and the air flow generation part may be provided in the housing, so dust or foreign matters on the surface of a shoe can be removed by the air flow generation part, and dehumidification, sterilization, and disinfection of the inside of the shoe can be performed by the care unit, thereby managing the shoe more hygienically.

Agitators may be used in the shoe management device, which may forcibly remove dust or foreign matters on the surface of a shoe while rotating. The agitators may be in close contact with the lower surface and the lower end portions of the side surfaces of the shoe, and fine dust on the surface of the shoe can be removed by an air flow provided by the air flow generation part. Cleaning of the outer portion of the shoe may be better performed.

In the shoe management device, the shoe may be inserted into the housing body having the inner space, which may be opened and/or closed by a cover. Dust, moisture, and bacteria on the shoe may be removed, and the removed dust, moisture, and bacteria may not be allowed to be transmitted to the outside. Accordingly, space in which the shoe management device is located may not be affected.

In addition to an ultraviolet lighting of a sterilization emitter, an operation performance part located in the care unit may provide plasma ions so as to perform sterilization and deodorization. Accordingly, the lighting of the sterilization emitter and the plasma ions act complementarily to each other, thereby enabling sterilization and deodorization inside the shoe to be more effectively performed.

It should be noted that in adding reference numerals to the components of each drawing, the same components have the same reference numerals when possible, even if they are displayed on different drawings. In addition, in describing the embodiments of the present disclosure, when it is determined that a detailed description of a related known configuration or function interferes with the understanding of the present disclosure, the detailed description is omitted.

In addition, in describing the components of the embodiments of the present disclosure, terms such as first, second, A, B, a, and b may be used. These terms are only for distinguishing the components from other components, and the nature, order, or order of each of the components is not limited to the terms. When a component is described as being "connected" or "coupled" to another component, that component may be directly connected to or coupled to the other component. However, it should be understood that another component may be "connected" or "coupled" to each component therebetween.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present invention.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A shoe management device comprising:
    a housing having an inner space configured to store at least a pair of shoes;
    an air flow generator provided in the inner space and configured to blow air toward the shoes; and
    a shoe dryer provided in the inner space and configured to be inserted into each of the pair of shoes,
    wherein the shoe dryer discharges:
        ultraviolet (UV) light to sterilize the shoes, and
        plasma ions to disinfect the shoes, and
    wherein the shoe dryer includes a body coupled to a rear of the housing and at least a pair of forward extensions protruding forward and configured to be inserted into the pair of shoes, respectively, each of the forward extensions having a UV light emitter and at least one discharge channel configured to discharge at least one of the plasma ions or hot air.

2. The device of claim 1, wherein the UV light emitter is provided at a front end of the forward extension, and the at least one discharge channel includes a first discharge channel provided on an upper surface of the forward extension and a second discharge channel provided on a lower surface of the forward extension.

3. The device of claim 2, wherein the first and second discharge channels are configured to discharge hot air and plasma ions simultaneously or sequentially.

4. The device of claim 1, wherein the body of the shoe dryer is U-shaped so as to have downward extensions extending downward, the forward extensions extending forward from the downward extensions, and the body further includes a handle protruding forward from a center of an upper portion.

5. The device of claim 1, further comprising a holding column mounted to the rear of the housing, the body of the shoe dryer being hung on the holding column, wherein the holding column is configured to have an adjustable height such that a height of the shoe dryer is adjusted.

6. The device of claim 1, further comprising a plurality of agitators provided at a bottom of the inner space and configured to rotate under the shoes, each of the agitators having a plurality of ribs provided at predetermined angular intervals on an outer circumferential surface, the ribs being made of a deformable material.

7. The device of claim 6, further comprising a tray provided under the agitators to collect foreign matter falling from the shoes, wherein the agitators are provided in at least a pair of columns to correspond to the pair of shoes, and the tray is configured to be inserted into and withdrawn from the housing to discard the collected foreign matter.

8. The device of claim 7, wherein the ribs extend between opposite ends of each of the agitators, each of ribs having a predetermined curvature.

9. The device of claim 6, further comprising an internal frame provided in the inner space to surround the agitators, a first support extending between opposite sides of the internal frame, and a second support extending between opposite ends of the internal frame to intersect with the first support, the first and second supports being configured to support the shoes.

10. The device of claim 9, wherein the agitators are provided in at least a pair of columns to correspond to the pair of shoes, curved portions are formed in the first support, which extends in a longitudinal direction of the columns in which the agitators are arranged, each of the curved portions being provided between adjacent agitators in a same column.

11. The device of claim 9, wherein curved grooves are formed in a bottom portion of the internal frame, the curved grooves being configured to avoid interference with the agitators.

12. The device of claim 6, wherein adjacent agitators are configured to rotate in opposite directions so as not to move the shoes in a single direction.

13. A shoe management device comprising:
    a housing having an inner space configured to store a plurality of shoes;
    a shoe dryer provided in the inner space and having a plurality of forward extensions configured to be inserted into the plurality of shoes, respectively, and to emit at least one of ultraviolet (UV) light or plasma ions to an inside of the shoes; and
    a plurality of agitators provided at a bottom of the inner space and configured to remove foreign matter from the shoes.

14. The device of claim 13, wherein the forward extensions include a UV light emitter provided at a front end, a first discharge port provided on an upper surface, and a second discharge port provided on a lower surface, the first and second discharge ports being configured to emit hot air and plasma ions simultaneously or sequentially.

15. The device of claim 13, wherein the shoe dryer comprises:
    a body, the plurality of forward extensions protruding forward from the body;
    a plurality of downward extensions extending downward from the body; and
    a handle protruding forward from a center of the body.

16. The device of claim 13, wherein the agitators are arranged in a plurality of columns to correspond to the plurality of shoes, and a tray is provided under the agitators to collect foreign matter, the tray being configured to be inserted into and withdrawn from the housing.

17. The device of claim 13, further comprising:
an internal frame provided in the inner space to surround the agitators,
a first support provided on the internal frame and extending in a forward-rearward direction, and
a second support provided on the internal frame and extending in a left-right direction to intersect with the first support, the first and second supports being configured to support the plurality of shoes.

18. The device of claim 13, further comprising a blower configured to blow air toward the shoes to remove foreign matter from the shoes.

\* \* \* \* \*